US008906038B2

(12) United States Patent
Ewers et al.

(10) Patent No.: US 8,906,038 B2
(45) Date of Patent: Dec. 9, 2014

(54) DEVICES AND METHODS FOR LAPAROSCOPIC GASTRIC TISSUE RECONFIGURATION

(75) Inventors: Richard C. Ewers, Fullerton, CA (US); Eugene G. Chen, Carlsbad, CA (US); Tracy D. Maahs, Yorba Linda, CA (US); Stuart Moran, San Clemente, CA (US); Cang C. Lam, Tustin, CA (US)

(73) Assignee: USGI Medical, Inc., San Clemente, CA (US)

( * ) Notice: Subject to any disclaimer, the term of this patent is extended or adjusted under 35 U.S.C. 154(b) by 270 days.

(21) Appl. No.: 13/033,485

(22) Filed: Feb. 23, 2011

(65) Prior Publication Data

US 2011/0208209 A1    Aug. 25, 2011

Related U.S. Application Data

(60) Provisional application No. 61/307,376, filed on Feb. 23, 2010.

(51) Int. Cl.
| | | |
|---|---|---|
| A61B 17/10 | (2006.01) | |
| A61B 17/08 | (2006.01) | |
| A61B 17/04 | (2006.01) | |
| A61B 17/42 | (2006.01) | |
| A61F 5/00 | (2006.01) | |
| A61B 17/00 | (2006.01) | |
| A61B 17/06 | (2006.01) | |
| A61B 17/29 | (2006.01) | |

(52) U.S. Cl.
CPC ............ *A61B 17/04* (2013.01); *A61B 17/0487* (2013.01); *A61F 5/0083* (2013.01); *A61B 2017/0496* (2013.01); *A61B 2017/00818* (2013.01); *A61B 2017/0464* (2013.01); *A61B 2017/06052* (2013.01); *A61B 2017/00867* (2013.01); *A61B 2017/0404* (2013.01); *A61B 2017/0488* (2013.01); *A61B 2017/00349* (2013.01); *A61B 2017/0409* (2013.01); *A61B 2017/0417* (2013.01); *A61B 2017/0419* (2013.01); *A61B 17/42* (2013.01); *A61B 2017/2926* (2013.01)
USPC ............................ 606/139; 606/153; 606/232

(58) Field of Classification Search
CPC .... A61B 17/04; A61B 17/0487; A61B 17/42; A61B 2017/00349; A61B 2017/00818; A61B 2017/00867; A61B 2017/0404; A61B 2017/0409; A61B 2017/0417; A61B 2017/0419; A61B 2017/0464; A61B 2017/0488; A61B 2017/06052; A61B 2017/2926
USPC ......... 606/139, 142, 143, 151, 153, 144, 148, 606/232; 128/898
See application file for complete search history.

(56) References Cited

U.S. PATENT DOCUMENTS 4,235,238 A * 11/1980 Ogiu et al. ..................... 606/145
5,254,126 A * 10/1993 Filipi et al. .................... 606/146
(Continued)

OTHER PUBLICATIONS

Office Action mailed Jul. 25, 2011 in U.S. Appl. No. 12/409,335.
(Continued)

*Primary Examiner* — Julian W Woo
(74) *Attorney, Agent, or Firm* — Kenneth H. Ohriner; Perkins Coie LLP

(57) ABSTRACT

Devices and methods for forming and securing tissue folds and elongated invaginations in gastric tissue are used as a treatment for obesity. In several embodiments, a plurality of tissue folds is formed along the greater curvature of the stomach using laparoscopic tissue anchor deployment devices. Additional embodiments include various combinations of tissue folds, elongated invaginations, and other reconfigurations of stomach tissue using laparoscopic devices or laparoscopic devices in combination with endoscopic devices.

13 Claims, 20 Drawing Sheets

(56) References Cited

U.S. PATENT DOCUMENTS

| | | | |
|---|---|---|---|
| 5,269,809 A * | 12/1993 | Hayhurst et al. | 606/232 |
| 5,464,426 A * | 11/1995 | Bonutti | 606/232 |
| 6,152,935 A * | 11/2000 | Kammerer et al. | 606/144 |
| 6,835,199 B2 * | 12/2004 | McGuckin et al. | 606/142 |
| 7,090,684 B2 * | 8/2006 | McGuckin et al. | 606/139 |
| 7,347,863 B2 * | 3/2008 | Rothe et al. | 606/139 |
| 7,361,180 B2 | 4/2008 | Saadat et al. | |
| 7,416,554 B2 | 8/2008 | Lam et al. | |
| 7,601,159 B2 * | 10/2009 | Ewers et al. | 606/139 |
| 7,621,925 B2 | 11/2009 | Saadat et al. | |
| 7,678,135 B2 | 3/2010 | Maahs et al. | |
| 7,704,264 B2 | 4/2010 | Ewers et al. | |
| 7,736,372 B2 | 6/2010 | Reydel et al. | |
| 7,736,374 B2 * | 6/2010 | Vaughan et al. | 606/153 |
| 7,744,613 B2 | 6/2010 | Ewers et al. | |
| 7,846,180 B2 * | 12/2010 | Cerier | 606/232 |
| 7,909,851 B2 * | 3/2011 | Stone et al. | 606/232 |
| 7,942,884 B2 | 5/2011 | Vahid et al. | |
| 7,955,340 B2 | 6/2011 | Michlitsch et al. | |
| 8,057,490 B2 * | 11/2011 | Harris et al. | 606/139 |
| 8,087,413 B2 | 1/2012 | Saadat et al. | |
| 8,216,253 B2 | 7/2012 | Saadat et al. | |
| 8,216,260 B2 | 7/2012 | Lam et al. | |
| 8,236,009 B2 | 8/2012 | Saadat et al. | |
| 8,257,394 B2 * | 9/2012 | Saadat et al. | 606/232 |
| 8,262,676 B2 | 9/2012 | Ewers et al. | |
| 2004/0162568 A1 | 8/2004 | Saadat et al. | |
| 2005/0250980 A1 | 11/2005 | Swanstrom et al. | |
| 2008/0208216 A1 | 8/2008 | Cerier | |
| 2008/0319455 A1 * | 12/2008 | Harris et al. | 606/139 |
| 2009/0275980 A1 * | 11/2009 | Zeiner et al. | 606/232 |

OTHER PUBLICATIONS

Office Action mailed Oct. 31, 2011 in U.S. Appl. No. 12/409,335.

* cited by examiner

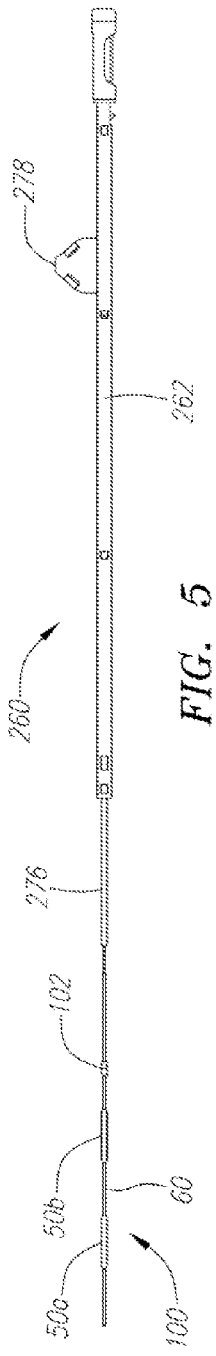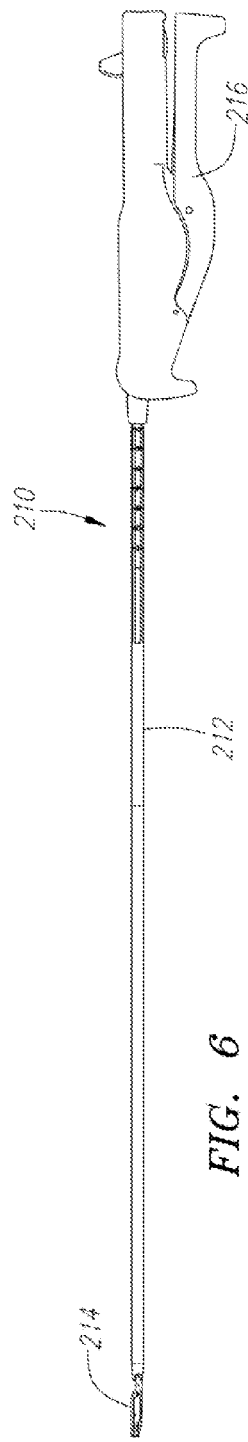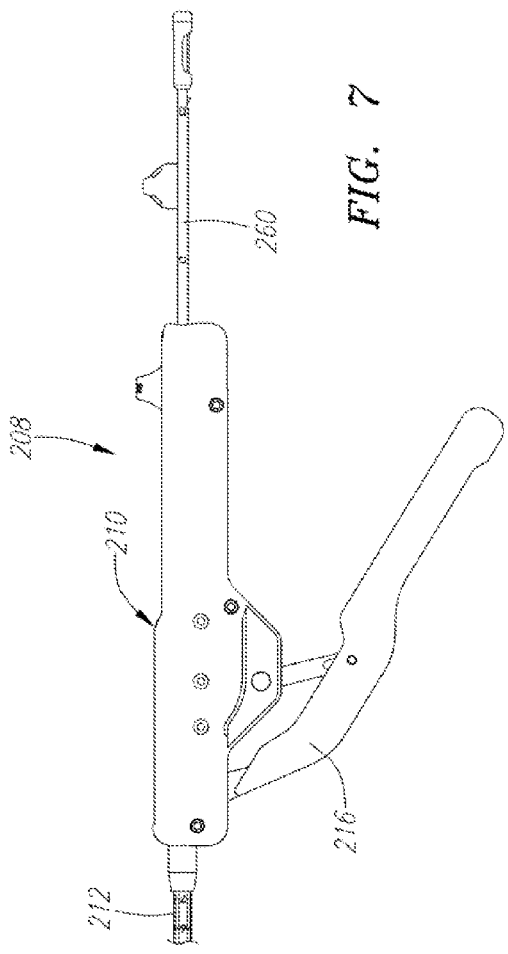

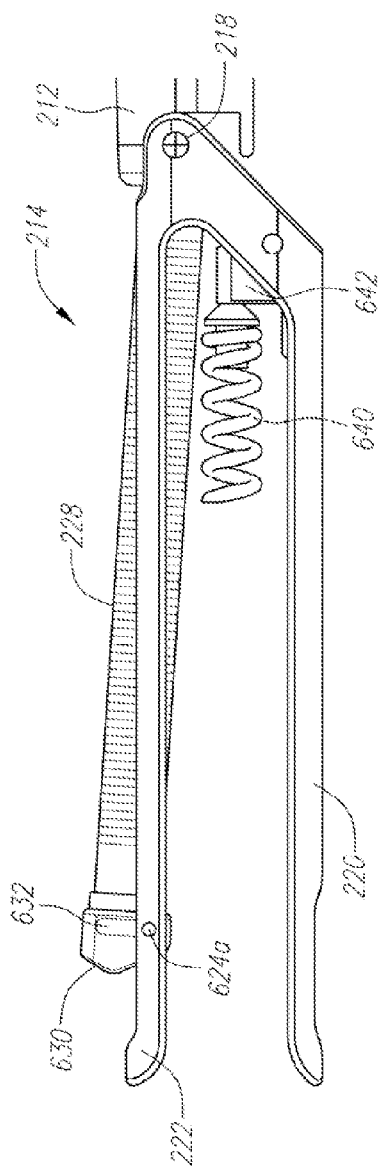
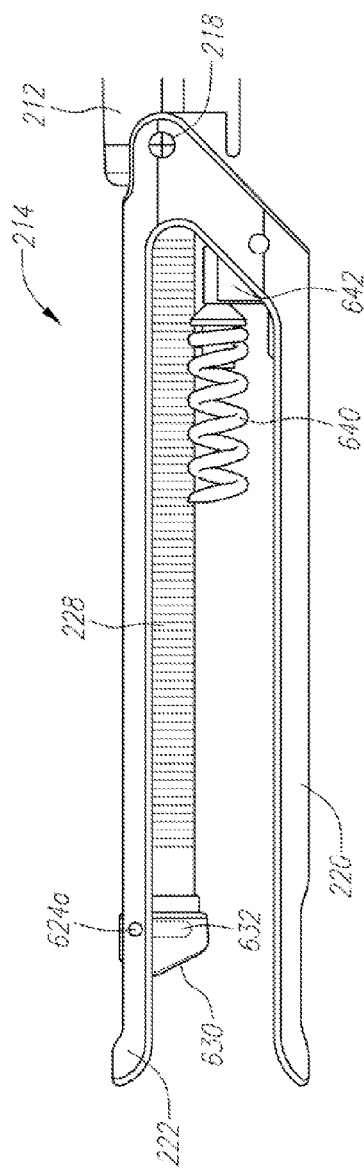
FIG. 9F
FIG. 9G

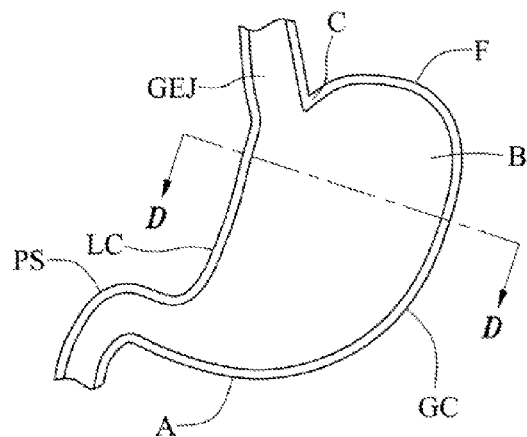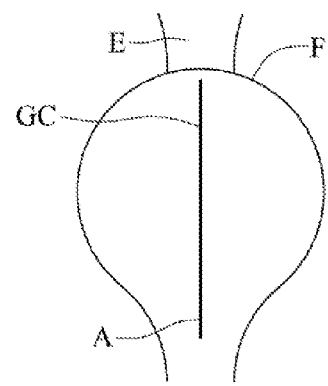
FIG. 14     FIG. 15
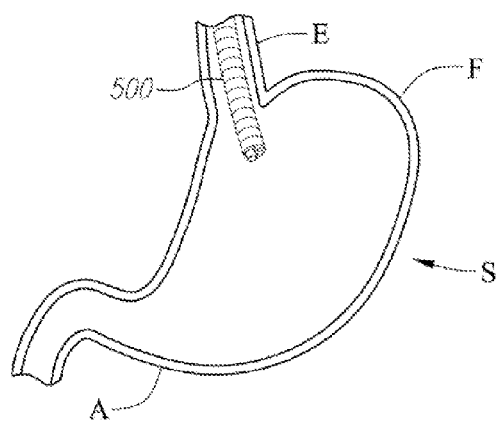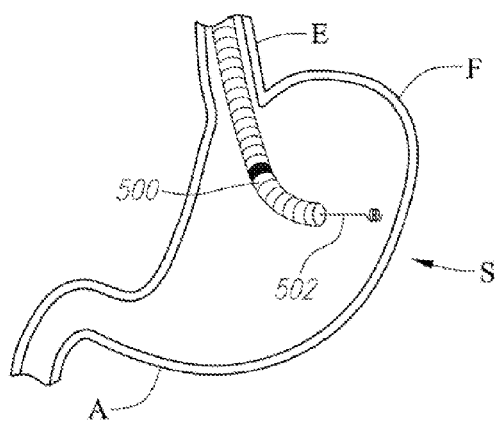
FIG. 16     FIG. 17

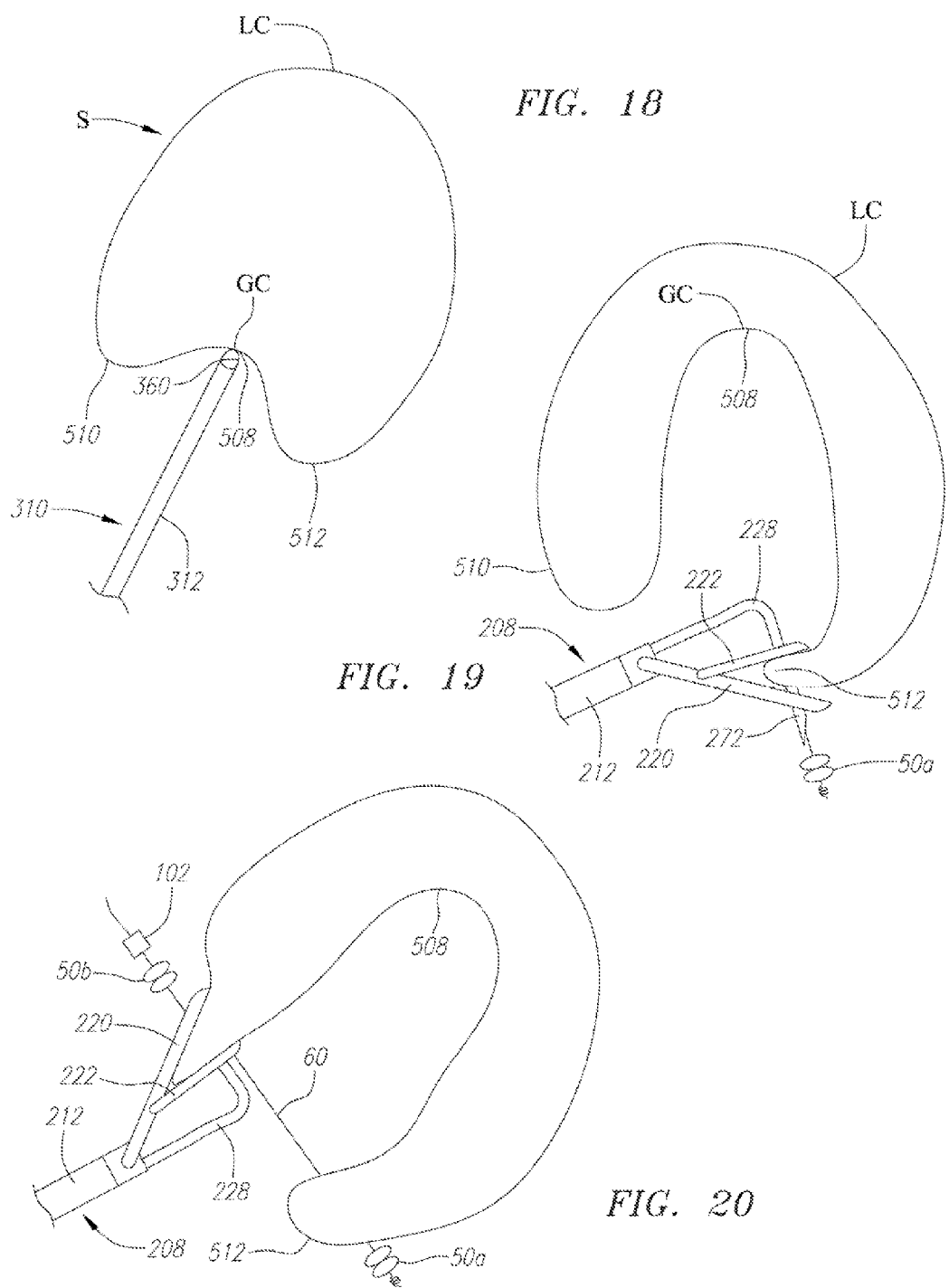

DEVICES AND METHODS FOR LAPAROSCOPIC GASTRIC TISSUE RECONFIGURATION

CROSS-REFERENCE TO RELATED APPLICATIONS

This application claims the benefit of priority to U.S. Provisional Patent Application No. 61/307,376, filed on Feb. 23, 2010, the contents of which are incorporated herein by reference in their entirety. This application also relates to U.S. Provisional Patent Application Ser. No. 61/239,709, filed on Sep. 3, 2009, U.S. Provisional Patent Application Ser. No. 61/432,537, filed Jan. 13, 2011, U.S. patent application Ser. No. 12/409,335, filed on Mar. 23, 2009, U.S. patent application Ser. No. 12/486,578, filed on Jun. 17, 2009, and U.S. patent application Ser. No. 12/876,029, filed Sep. 3, 2010, the contents of each of which are incorporated herein by reference in their entireties.

BACKGROUND

The present disclosure pertains to devices and methods for laparoscopic gastric tissue reconfiguration. More particularly, the present disclosure relates to devices and methods for laparoscopically manipulating stomach tissue, forming and securing tissue folds, forming and securing tissue invaginations, altering stomach tissue configuration, restricting the ability of stomach tissue to distend, altering the function of nerves located in or near stomach tissue, and/or altering hormone production from cells associated with stomach tissue. The devices and methods described herein have particular application to methods and treatments for obesity.

The National Institutes of Health (NIH) estimate that about two-thirds of adults—133.6 million people—in the U.S. are overweight or obese, while almost 5% of adults—15 million Americans—are considered extremely obese. Obese adults are at increased risk of type II diabetes, hypertension, stroke, certain cancers, and other dangerous conditions.

The NIH estimates that being overweight or obese leads to $117 billion in medical spending a year, with $61 billion in direct costs and $56 billion in indirect costs.

As obesity rates continue to rise, patients are increasingly seeking surgical weight loss options. Bariatric surgery aids weight loss by restricting food intake and, in some operations, altering the digestive process. The Roux-en-Y Gastric Bypass Procedure (RYGBP) is the most commonly performed bariatric procedure, estimated to account for approximately 65% of weight loss surgeries performed in the U.S.

A study from the Agency for Healthcare Research and Quality (AHRQ) found that the number of bariatric surgeries grew by 400 percent between 1998 and 2002. In 2007, an estimated 205,000 people with morbid obesity in the U.S. underwent bariatric surgery and these numbers are expected to grow. Only 1% of the clinically eligible population is currently being treated for morbid obesity through bariatric surgery.

A major retrospective study published in the New England Journal of Medicine showed that gastric bypass reduced the risk of death in extremely obese patients by over 40% by lowering the incidence of diabetes, coronary artery disease and cancer.

The Roux-en-Y gastric bypass procedure involves creating a small stomach pouch out of a portion of the stomach and attaching it directly to the jejunum, bypassing a large part of the stomach and duodenum. The stomach is made very small to restrict the amount of food that can be consumed. The opening between the stomach pouch and the small intestine (called the stoma) is also made very small to slow the passage of food from the stomach. These restrictions help the patient feel full and limit the amount of food that can be eaten. In addition, by altering the path of the intestines, consumed food bypasses the duodenum so fat absorption is substantially reduced.

The RYGB procedure is performed either laparoscopically or in an open surgery. Alternative procedures for obtaining some or all of the benefits of the RYGB procedure with fewer of the associated complications, risks, limitations, and costs would be preferred.

SUMMARY

In a first aspect, laparoscopic treatment of obesity includes a number of methods and devices. The devices are introduced laparoscopically (e.g., via one or more trocars, etc.) into the patient's body and into the peritoneal cavity to approach the exterior of the stomach at or near the greater curvature. The stomach is then mobilized by dissecting the connecting tissue (e.g., greater omentum) attached to the stomach. Once the instruments are positioned near the exterior of the greater curvature of the stomach, the external tissue of the stomach is temporarily engaged and/or grasped and the engaged tissue is manipulated by a surgeon or practitioner from outside the patient's body.

In engaging, manipulating, and/or securing the tissue, various methods and devices may be implemented. For instance, tissue securement devices may be delivered and positioned through the abdominal wall via one or more trocars. The tissue securement devices include end effectors suitable for contacting the exterior stomach wall, manipulating stomach tissue, creating one or more tissue folds, and/or deploying one or more tissue anchors through the tissue fold(s). The tissue anchor(s) extending on a connecting member (e.g., a suturing element) may be disposed through at least the serosa layers of the stomach wall. A tissue manipulation assembly positioned at the distal end of a tissue securement device may be used for engaging the tissue and deploying the tissue anchor to secure the tissue with the tissue anchor. A second tissue anchor may then be deployed in a second tissue fold, after which the tissue folds are brought into apposition by decreasing the length of the connecting member extending between the two tissue anchors. In some embodiments, this is done by advancing an uni-directional cinching element along the connecting member.

In some embodiments, the foregoing method is repeated at a plurality of locations along the greater curvature of the stomach extending between the fundus and the antrum to thereby form an extended invagination of the stomach. This extended invagination has as one effect the reduction of stomach volume.

In some embodiments, an endoscope or other device is advanced through a patient's mouth and esophagus and into the patient's stomach. The endoscope is used to provide visualization, insufflation, and/or other functional features desired by the user. One or more endoscopic instruments may be advanced through a working channel of the endoscope or other access device and extended from a distal end thereof to assist with the laparoscopic methods described above.

In some embodiments, the extended invagination is located substantially along the greater curvature of the stomach. In other embodiments, the extended invagination is located substantially on the anterior wall of the stomach. In still other embodiments, two or more extended invaginations are formed in the body region of the stomach along the greater curvature, the anterior wall, and/or the posterior wall.

In alternative embodiments, various combinations of tissue folds, extended invaginations, and other tissue reconfigurations are formed and secured at selected regions of the stomach. The tissue folds, invaginations, and other reconfigurations have the effects of reducing stomach volume, inhibiting distention of stomach tissue, more effectively and more quickly forcing food distally to the antrum, and/or favorably altering the nerve function and/or hormone production of stomach tissue to thereby create signals of satiety.

BRIEF DESCRIPTION OF THE DRAWINGS

FIG. 5 is a side view of a third embodiment of an anchor deployment catheter.

FIG. 6 is a side view of a laparoscopic tissue manipulation and anchor deployment device.

FIG. 7 is a side view of a first embodiment of a handle portion of the laparoscopic tissue manipulation and anchor deployment device of FIG. 6.

FIGS. 9A through 9G are perspective and side views of embodiments of end effectors of the laparoscopic tissue manipulation and anchor deployment device of FIG. 6.

FIG. 14 is a cross-sectional anterior side view of a human stomach.

FIG. 15 is a side view of the stomach shown in FIG. 14 viewed from the side of the Greater Curvature.

FIGS. 16 and 17 are cross-sectional anterior side views of a human stomach.

FIGS. 18 through 23 are cross-sectional top views taken along line D-D of the human stomach shown in FIG. 14 illustrating a progression of a laparoscopic stomach tissue reconfiguration procedure.

DETAILED DESCRIPTION

Laparoscopic surgical devices and methods for engaging, manipulating, reconfiguring, and securing stomach tissue are described herein. In several embodiments, the methods entail performing surgery through one or a limited number of trocars, eliminating the need for an open surgical procedure. Laparoscopic procedures provide faster healing times, less scarring, and less pain which could lead to reduced hospitalization and quicker recovery in comparison to most open surgical procedures.

In several embodiments, the laparoscopic surgical procedures are performed using devices that have been developed by USGI Medical, Inc. of San Clemente, Calif. Several tissue manipulation and tissue anchor delivery devices are described in the following United States patent applications:

TABLE 2

| U.S. patent application Ser. No. | Filing Date |
| --- | --- |
| 10/612,109 | Jul. 1, 2003 |
| 10/639,162 | Aug. 11, 2003 |
| 10/672,375 | Sep. 26, 2003 |
| 10/734,547 | Dec. 12, 2003 |
| 10/734,562 | Dec. 12, 2003 |
| 10/735,030 | Dec. 12, 2003 |
| 10/840,950 | May 7, 2004 |
| 10/955,245 | Sep. 29, 2004 |
| 11/070,863 | Mar. 1, 2005 |
| 12/486,578 | Jun. 17, 2009 |
| 61/432,537 | Jan. 13, 2011 |

The foregoing applications describe several tissue manipulation and tissue anchor delivery devices and embodiments, including flexible devices used for endolumenal procedures. Several tissue anchor delivery devices suitable for laparoscopic use are described more fully below.

Endolumenal tissue grasping devices are described in several of the United States patent applications listed above, and in the following United States patent applications:

TABLE 3

| U.S. patent application Ser. No. | Filing Date |
| --- | --- |
| 11/736,539 | Apr. 17, 2007 |
| 11/736,541 | Apr. 17, 2007 |

Tissue anchors are described in several of the United States patent applications listed above, and in the following United States patent applications:

TABLE 4

| U.S. patent application Ser. No. | Filing Date |
| --- | --- |
| 10/841,411 | May 7, 2004 |
| 11/404,423 | Apr. 14, 2006 |
| 11/773,933 | Jul. 5, 2007 |

Each of the foregoing patent applications is hereby incorporated by reference in its entirety.

Tissue Anchors and Delivery Devices and Methods

Several embodiments of the laparoscopic surgical procedures described herein include the steps of grasping stomach tissue to form a tissue fold and deploying or implanting a fold retaining device (e.g., a tissue anchor assembly) that is used to maintain the fold. For simplicity, the discussion herein will describe tissue anchor assemblies holding tissue folds, with it being understood that other portions or sections of tissue that do not constitute tissue folds are suitably retained by the tissue anchor assemblies. The following sections include descriptions of several embodiments of devices that are suitable for performing these and other laparoscopic surgical procedures.

Figure 1:
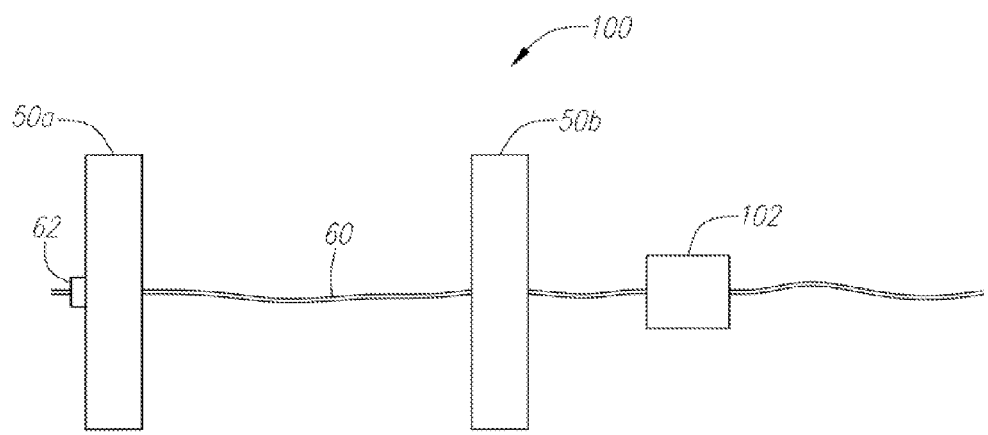
FIG. 1 is a schematic representation of a tissue anchor assembly.

In several embodiments, a tissue anchor assembly is used to maintain a tissue fold in the stomach tissue. The preferred tissue anchor assemblies include tissue anchors such as those described in several of the United States patent applications incorporated by reference above, including Ser. Nos. 10/841,411, 11/404,423, and 11/773,933. A schematic representation of a suitable tissue anchor assembly is shown in FIG. 1. Those skilled in the art will recognize that tissue anchors other than those described herein may be suitable for use in some embodiments. For example, "T"-type anchors or "T"-tags having a pair across members attached to each other by a connecting member are known in the art and may be suitable for use in the methods described herein.

Figure 2:
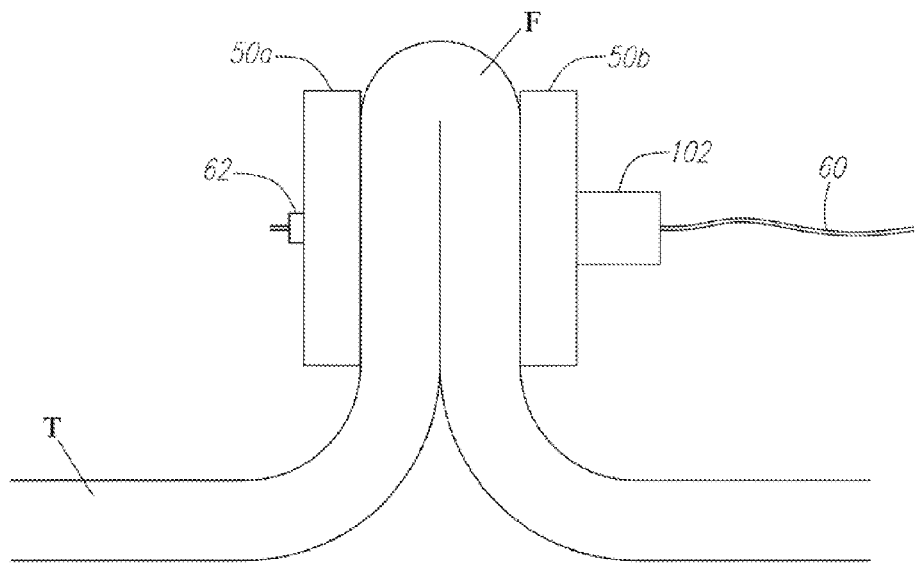
FIG. 2 is a schematic representation of a tissue anchor assembly securing a tissue fold.

Preferably, the tissue anchor assemblies include a pair of tissue anchors 50a, 50b slidably retained by a connecting member, such as a suture 60. A locking mechanism, such as a cinch 102, is also slidably retained on the suture 60. The cinch 102 is configured to be slidable on the suture 60 in only a single direction (one-way or uni-directional), in particular, toward the distal end of the suture. In this way, the cinch 102 is configured to provide a cinching force against the anchors 50a, 50b in order to impart a tension force on the suture. Accordingly, the tissue anchor assembly 100 is adapted to hold a fold of tissue, as shown in FIG. 2. In addition, as described below, the position of the cinch 102 on the suture 60 is able to be adjusted by the user during deployment of the tissue anchor assembly, thereby allowing the user to adjust the amount of tension force applied to the suture 60, and the amount of force that the anchors 50a, 50b impart to the tissue fold F.

Figure 8:
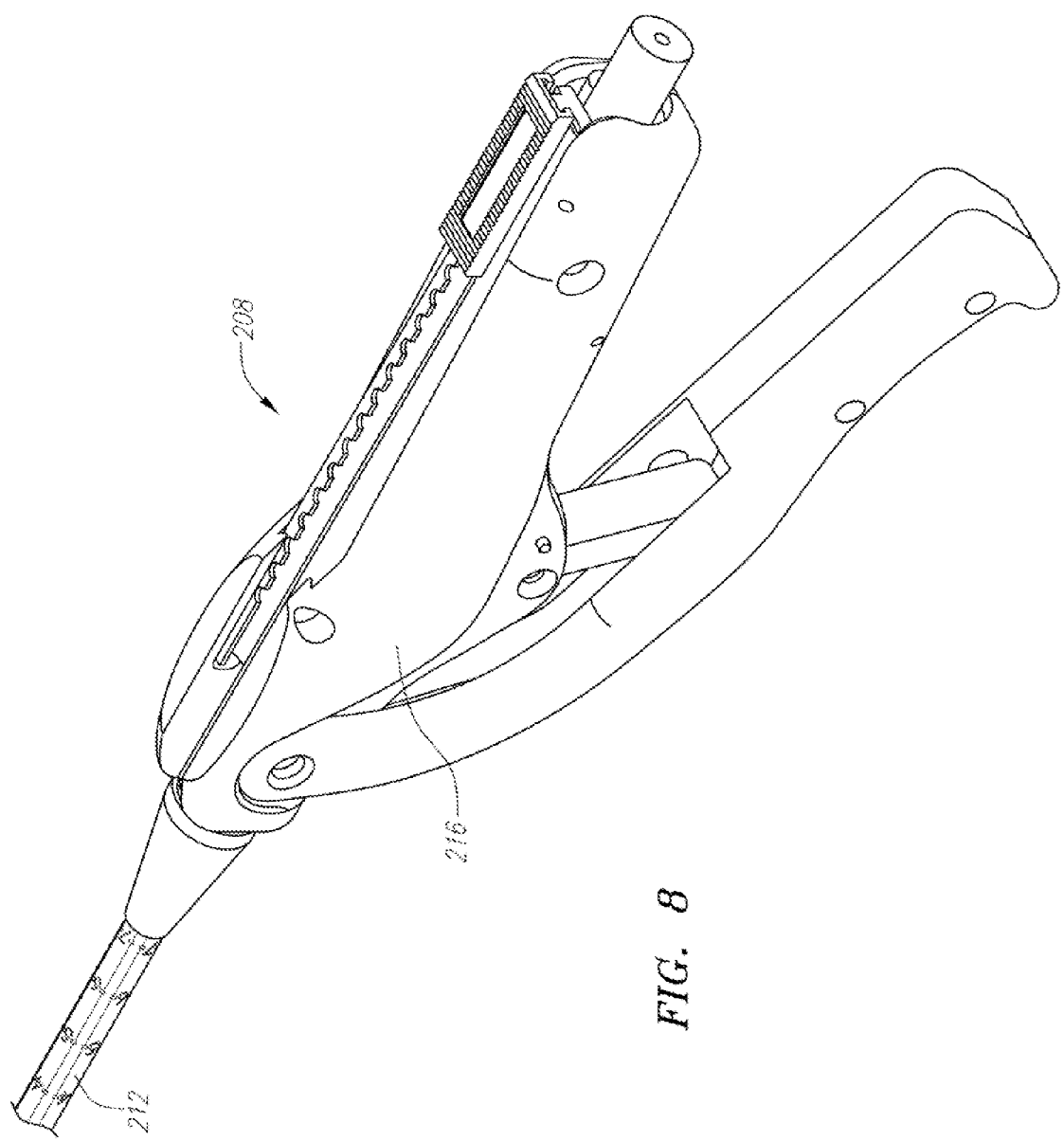
FIG. 8 is a perspective view of second embodiment of a handle portion of the laparoscopic tissue manipulation and anchor deployment device of FIG. 6.

In several embodiments, a delivery device is used to deploy the tissue anchors and tissue anchor assemblies 100 laparoscopically. An example of a suitable delivery device is shown in FIGS. 6-8. Embodiments of the device shown in FIGS. 6-8 but having a flexible shaft for use in endolumenal procedures are described in substantial detail in U.S. patent application Ser. Nos. 10/955,245, 11/070,863, 12/486,578, and 61/432,537, each of which is hereby incorporated by reference in its entirety (including all references cited therein) as if fully set forth herein. The laparoscopic embodiment of the delivery device 208 is described briefly below.

In manipulating tissue or creating tissue folds, a device having a handle 216, a substantially rigid shaft 212, and a distal end effector 214 is advanced laparoscopically, e.g., via a trocar, etc., into the patient's body, e.g., through the abdominal wall and into the peritoneal cavity. The end effector 214 is moved to the site of the target tissue, e.g., the external surface of the stomach. The stomach tissue may be engaged or grasped and the engaged tissue may be manipulated by a surgeon or practitioner from outside the patient's body. Examples of creating and forming tissue plications are described in further detail in the '245, '863, '578, and '537 applications incorporated by reference above.

Figure 3:
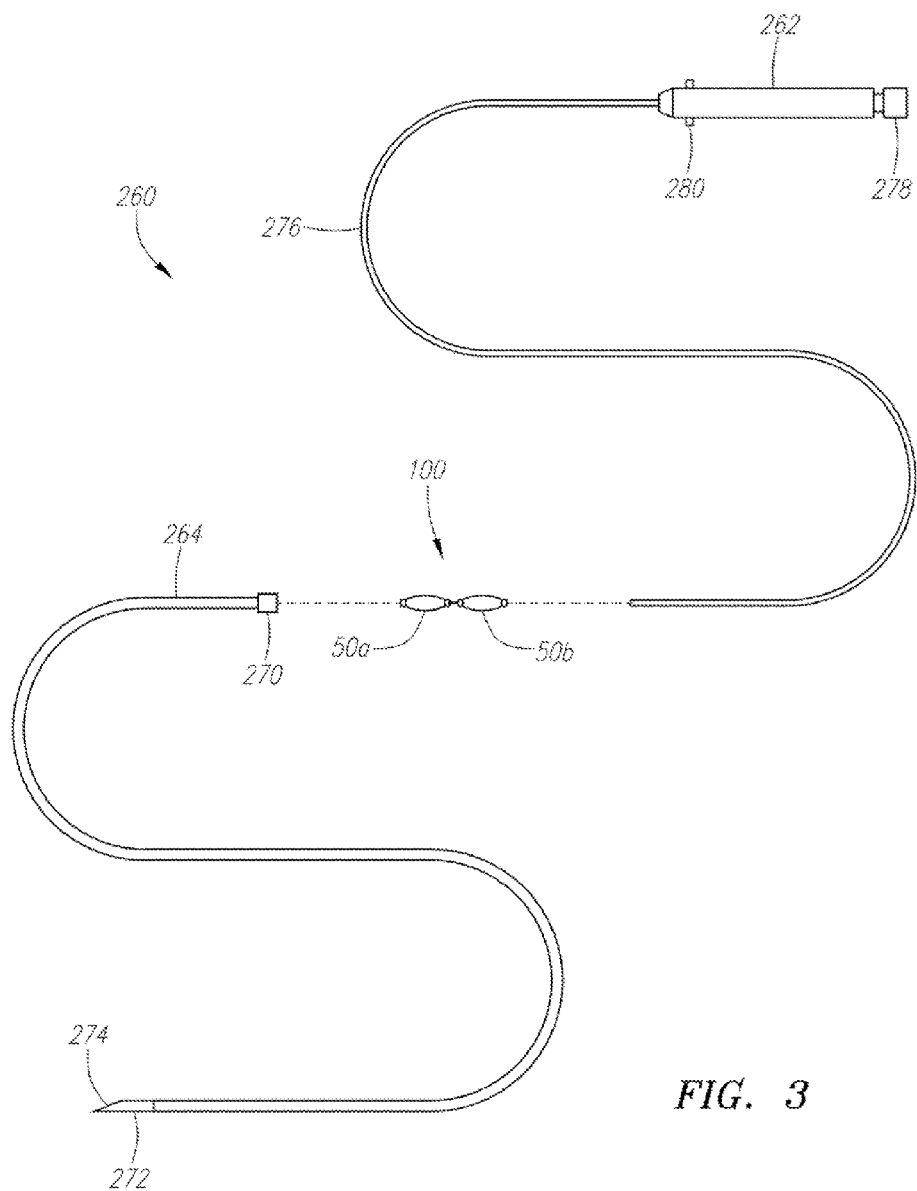
FIG. 3 is an exploded view of a first embodiment of an anchor deployment catheter.
Figure 4:
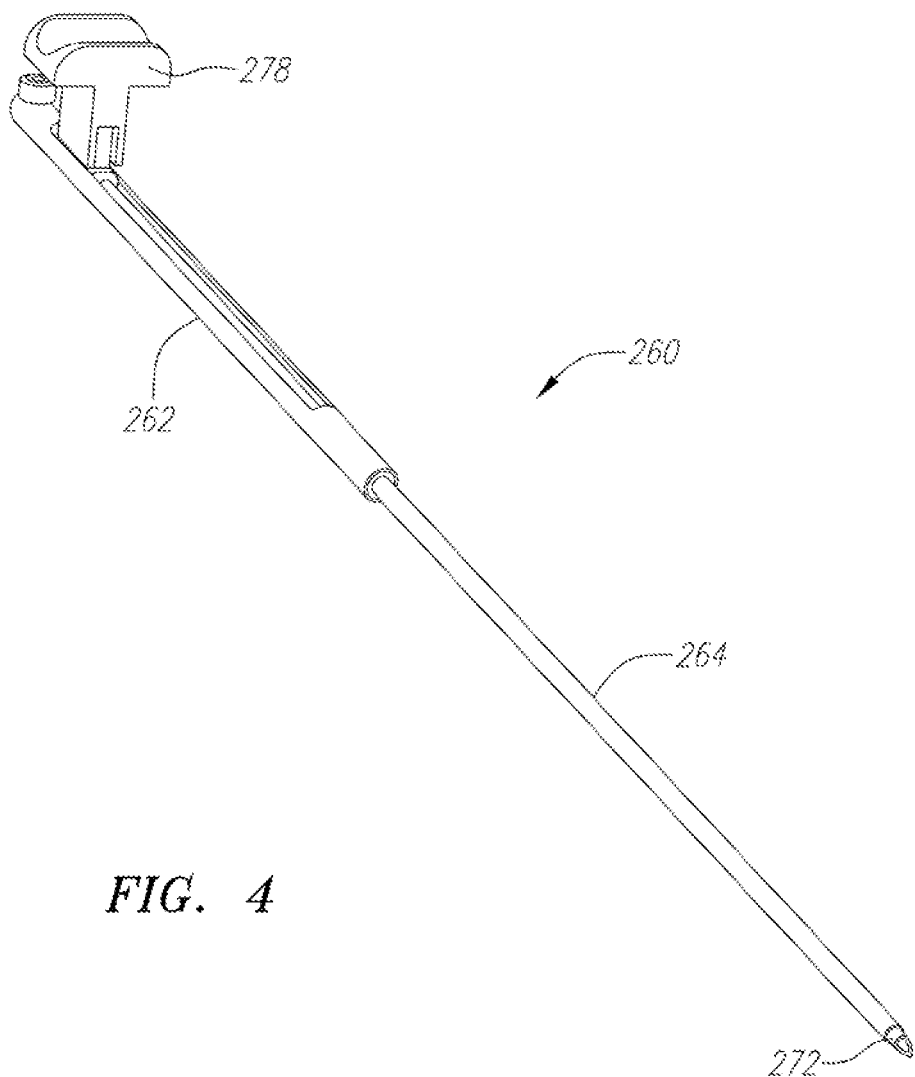
FIG. 4 is a perspective view of a second embodiment of an anchor deployment catheter.

The delivery device 208 shown in FIGS. 6-8 generally comprises a tissue manipulation assembly 210 and a needle deployment assembly 260. (Embodiments of the needle deployment assembly 260 are shown in FIGS. 3-5 and are described more fully below). The tissue manipulation assembly 210 includes a catheter or tubular body 212 that is configured to be substantially rigid for laparoscopic advancement via a trocar into the peritoneal cavity. The tubular body 212 is configured to be torqueable through various methods, e.g., utilizing a stainless steel or other substantially rigid tubular construction, such that when a handle 216 is manipulated and/or rotated by a practitioner from outside the patient's body, the longitudinal and/or torquing force is transmitted along the body 212 such that the distal end of the body 212 is advanced, withdrawn, or rotated in a corresponding manner.

A tissue manipulation end effector 214 is located at the distal end of the tubular body 212 and is generally used to contact and form tissue folds and/or to otherwise bring portions of tissue into apposition. Several embodiments of the distal end effector are shown in FIGS. 9A-G. In some embodiments, the tissue manipulation end effector 214 is connected to the distal end of the tubular body 212 via a pivotable coupling 218. A lower jaw member 220 extends distally from the pivotable coupling 218 and an upper jaw member 222, in this example, is pivotably coupled to the lower jaw member 220 via a jaw pivot 226. The location of the jaw pivot 226 may be positioned at various locations along the lower jaw 220 depending upon a number of factors, e.g., the desired size of the "bite" or opening for accepting tissue between the jaw members, the amount of closing force between the jaw members, etc. In other embodiments, the end effector 214 is connected to the distal end of the tubular body in a non-pivoting manner in which the lower jaw 220 is fixedly attached to the tubular body 212. One or both jaw members 220, 222 may optionally include a number of protrusions, projections, grasping teeth, textured surfaces, etc. on the surface or surfaces of the jaw members 220, 222 facing one another to facilitate the adherence of tissue between the jaw members 220, 222. In alternative embodiments, the surfaces of the jaw member 220, 222 are provided with a smooth, textured, or other atraumatic surface in order to decrease or eliminate the incidence of tissue injury.

Figure 9A:
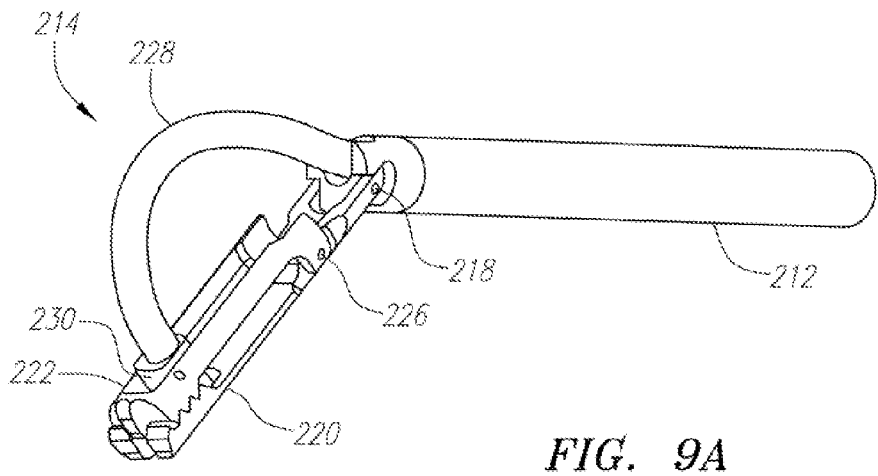
Figure 9B:
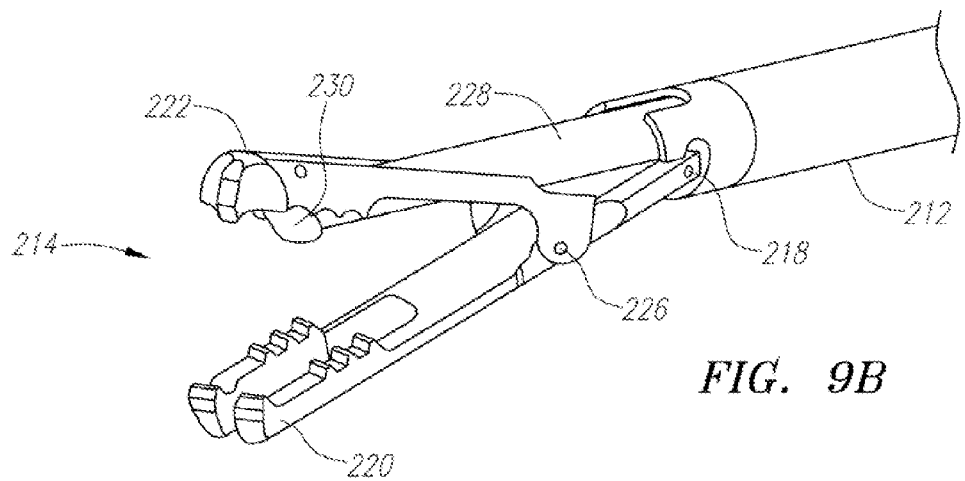
Figure 9C:
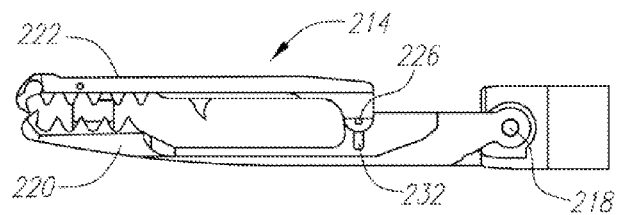
Figure 9D:
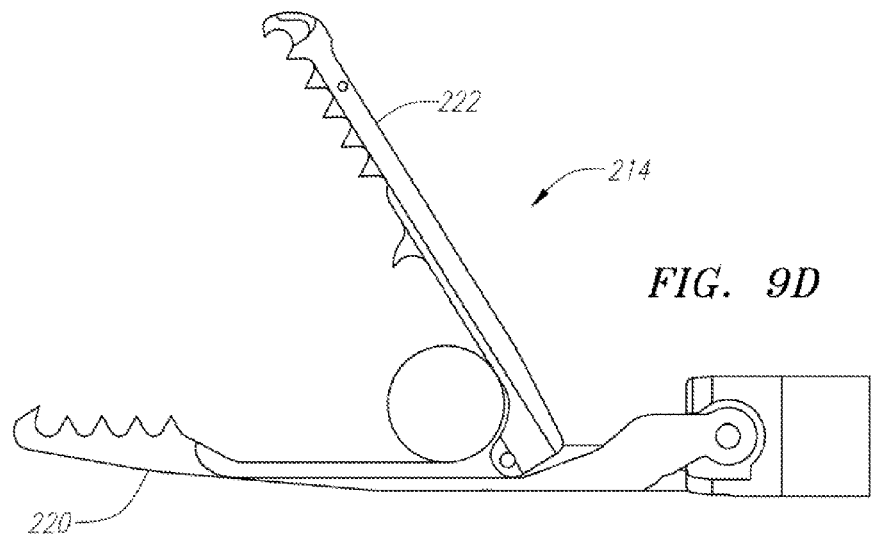
Figure 9E:
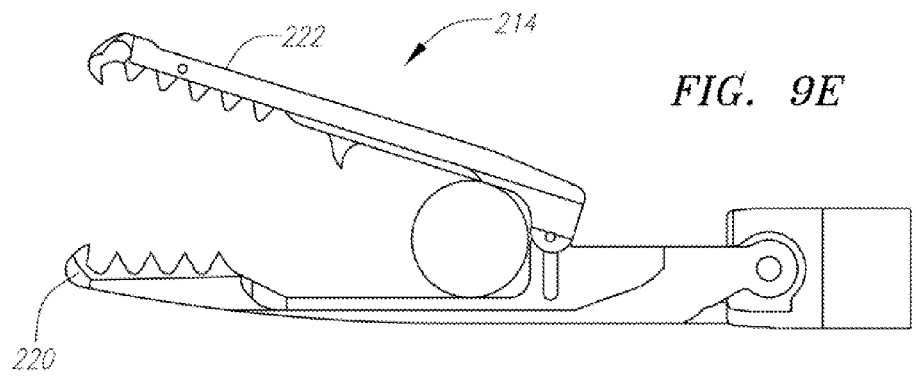

Turning to FIGS. 9C-E, three additional embodiments of the tissue manipulation end effector 214 are shown. For clarity, the tubular body 212 and launch tube 228 are not shown in the drawings. In the embodiment shown in FIG. 9D, the upper jaw 222 is pivotably coupled to the lower jaw 220 via a jaw pivot 226 that is fixedly attached to the lower jaw 220, as described above in relation to FIGS. 9A-B. In the embodiment shown in FIGS. 9C and 9E, a slotted jaw construction includes a jaw pivot 226 that is able to slide within an upright slot 232 formed in the frame of the lower jaw 220. In an alternative embodiment not shown, the jaw pivot 226 is fixed to the lower jaw 220 and slides within a slot 232 formed on the frame of the upper jaw 222. The capability of the jaw pivot 226 to slide within the upright slot 232 provides the end effector 214 with adjustable jaw geometries to better accommodate tissue folds (or other targets) having a wider range of sizes. For example, as shown by the illustrations in FIGS. 9D-E, the end effector 214 embodiment having the upright slot 232 (shown in FIG. 9E) is able to accommodate a comparably-sized target located at the vertex between the upper jaw 222 and lower jaw 220 without having to be opened as widely as is necessary with the end effector 214 embodiment that does not have the upright slot (shown in FIG. 9D).

Those skilled in the art will recognize that the slotted jaw construction described above and shown in FIGS. 9C and 9E is adaptable for use in other laparoscopic instruments (or other instruments) having a pair of jaws oriented to grasp, trap, or engage tissue or other materials between the jaws. For example, the slotted jaw construction may be adapted for use with a laparoscopic stapling device in order to provide improved orientation between an upper staple cartridge and a lower anvil portion of the device. Other uses of the slotted jaw construction are also possible.

In the embodiments described above, a distal end of the launch tube 228 is pivotally connected to the upper jaw member 222 at a launch tube pivot 230. The launch tube pivot 230 is pivotable around an axis defined by a pin that is attached to the upper jaw member 222 and that extends through a hole in the pivot 230. In several other embodiments, shown in FIGS. 9F-G, an alternative pivot 630 is provided that is capable of ranges of motion in addition to pivoting relative to the upper jaw member 222. For example, FIGS. 9F-G show alternative embodiments of an end effector 214 that includes a lower bail 220 having a distal slot 621 and an upper bail 222 having a distal slot 623. The lower bail 220 and upper bail 222 are maintained in a fixed spatial relationship relative to one another and are connected to the tubular body 212 by a pivotable coupling 218. A helical grasper 640 having a tissue piercing tip is movably retained within a slider 642 that slides in a slot formed in the lower fixed bail 220. The helical grasper 640 includes a shaft that extends proximally to the handle 216 of the anchor delivery device 208, where it is actuable by the user. The helical grasper 640 is able to be moved proximally and distally under the control of the user, as guided by the slider 642. In this way, the helical grasper 640 may be used to grasp tissue and retract the tissue into the space defined between the lower fixed bail 220 and the upper fixed bail 222.

A pivot 630 is pivotably and slidably connected to the upper fixed bail 222 via a pair of pivot pins 624a, 624b that are formed on the upper fixed bail 222. The pivot pins 624a, 624b are formed on opposing sides of a slot defined by the upper fixed bail 222, and define a pivot axis about which the pivot 630 is able to rotate. In a first embodiment, shown in FIGS. 9F-G, the pivot 630 includes two pivot slots 632 formed on opposite sides of the external surface of the pivot. Each pivot slot 632 has an elongated shape defined by a pivot slot upper end and a pivot slot lower end. The pivot 630 has a width that is slightly less than the width of the slot defined in the upper fixed bail 222. Accordingly, the pivot pins 624a, 624b are able to reside within the spaces defined by the pivot slots 632 formed on each side of the pivot 630. In this way, the pivot 630 is able to rotate (pivot) around the axis defined by the pivot pins 624a, 624b, and the body of the pivot 630 is also able to slide relative to the axis defined by the pivot pins 624a, 624b a distance defined by the length of the pivot slots 632. In this way, the pivot 630 may be rotated around the axis defined by the pivot pins 624a, 624b, and/or the pivot 630 may be moved into and out of the space between the lower fixed bail 220 and upper fixed bail 222 and/or proximally and distally relative to axis defined by the pivot pins 624a, 624b (depending upon the orientation of the pivot 630 relative to the upper fixed bail 222).

A launch tube 228 extends from the handle 216, through the tubular body 212, and distally from the end of the tubular body 212 where a distal end of the launch tube 228 is pivotally connected to the upper jaw member 222 at a launch tube pivot 230. A distal portion of the launch tube 228 may be pivoted into position within a channel or groove defined in the upper jaw member 222, to facilitate a low-profile configuration of the tissue manipulation end effector 214. When articulated, either via the launch tube 228 or other mechanism, the jaw members 220, 222 are urged into an open configuration to receive tissue in the opening between the jaw members 220, 222.

The launch tube 228 may be advanced from its proximal end at the handle 216 such that the portion of the launch tube 228 that extends distally from the tubular body 212 is forced to rotate at a hinge or pivot 230 and reconfigure itself such that the exposed portion forms a curved or arcuate shape that positions the launch tube opening perpendicularly relative to the upper jaw member 222. The launch tube 228, or at least the exposed portion of the launch tube 228, may be fabricated from a highly flexible material or it may be fabricated, e.g., from Nitinol tubing material which is adapted to flex, e.g., via circumferential slots, to permit bending.

Figure 10:
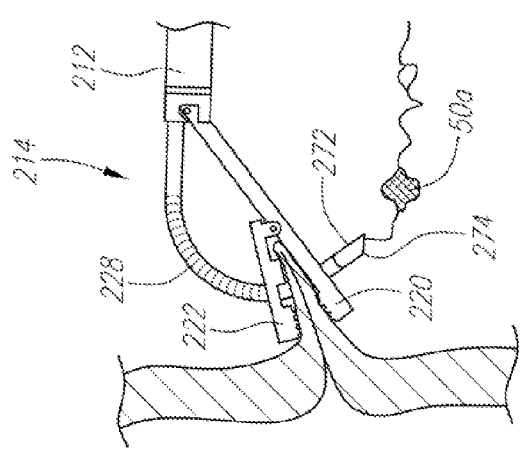
FIG. 10 is a side view of the distal end effector of an embodiment of the laparoscopic tissue manipulation and anchor deployment device of FIG. 6 deploying a tissue anchor assembly through a tissue fold.

Once the tissue has been engaged between the jaw members 220, 222, a needle deployment assembly 260 is urged through the handle 216, though the tubular body 212, and out through the launch tube 228. Embodiments of the needle deployment assembly are shown in FIGS. 3-5, and are described in substantial detail in U.S. patent application Ser. Nos. 10/955,245, 11/070,863, and 12/486,578, which are hereby incorporated by reference in their entireties (including all references cited therein) as if fully set forth herein. The needle deployment assembly 260 may pass through the lower jaw member 220 via a needle assembly opening (not shown in the drawings) defined in the lower jaw member 220 to pierce through the grasped tissue. Once the needle deployment assembly has been passed through the engaged tissue, one or more tissue anchors 50a of a tissue anchor assembly 100 (see FIG. 10) are deployed for securing the tissue, as described in further detail herein and in U.S. patent application Ser. No. 10/955,245, which has been incorporated by reference above.

Referring to FIGS. 3-5, each shows additional details relating to embodiments of a needle deployment assembly 260. As mentioned above, a needle deployment assembly 260 may be deployed through the tissue manipulation assembly 210 by introducing the needle deployment assembly 260 into the handle 216 and through the tubular body 212 such that the needle deployment assembly 260 is advanced from the launch tube 228 and into or through approximated tissue. Once the needle deployment assembly 260 has been advanced through the tissue, the anchor assembly 100 may be deployed or ejected. The anchor assembly 100 is normally positioned within the distal portion of a tubular sheath 264 that extends from a needle assembly control or housing 262. Once the anchor assembly 100 has been fully deployed from the sheath 264, the spent needle deployment assembly 260 may be removed from the tissue manipulation assembly 210 and another needle deployment assembly may be introduced without having to remove the tissue manipulation assembly 210 from the patient. The length of the sheath 264 is such that it may be passed entirely through the length of the tubular body 212 to enable the deployment of the needle deployment assembly 260 into and/or through the tissue.

The elongate sheath or catheter 264 extends removably from the needle assembly control or housing 262. The sheath or catheter 264 and the housing 262 may be interconnected via an interlock 270 which may be adapted to allow for the securement as well as the rapid release of the sheath 264 from the housing 262 through any number of fastening methods, e.g., threaded connection, press-fit, releasable pin, etc. The needle body 272, which may be configured into any one of the variations described above, extends from the distal end of the sheath 264 while maintaining communication between the lumen of the sheath 264 and the needle opening 274.

An elongate pusher 276 comprises a flexible wire, coil, or hypotube that is translationally disposed within the sheath 264 and movably connected within the housing 262. A proximally-located actuation member 278 is rotatably or otherwise connected to the housing 262 to selectively actuate the translational movement of the elongate pusher 276 relative to the sheath 264 for deploying the anchors from the needle opening 274. The tissue anchor assembly 100 is positioned distally of the elongate pusher 276 within the sheath 264 for deployment from the sheath 264. Needle assembly guides 280 protrude from the housing 262 for guidance through the locking mechanism described above.

Figure 11:
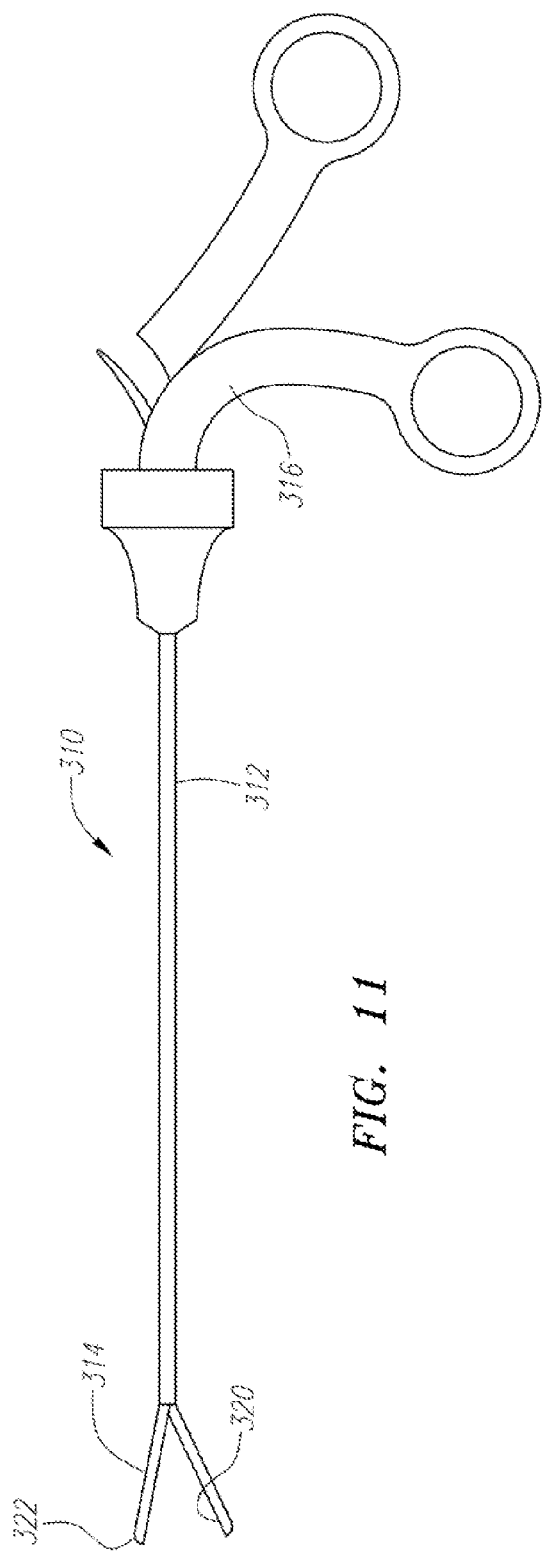
FIG. 11 is a side view of a laparoscopic instrument.
Figure 12A:
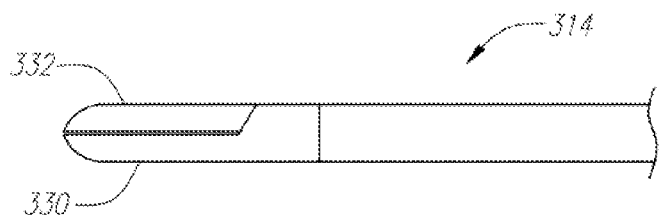
FIGS. 12A through 12D are side views of alternative end effectors for the laparoscopic instrument of FIG. 11.
Figure 12B:
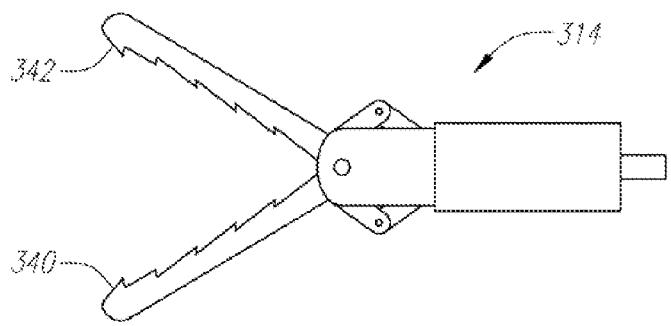
Figure 12C:
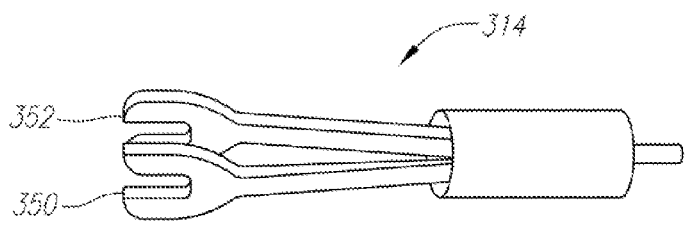
Figure 12D:
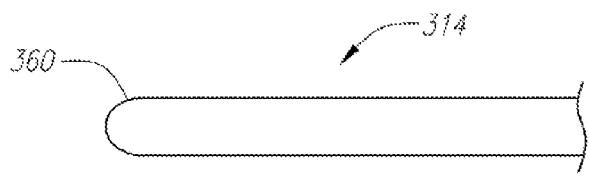

The laparoscopic tissue anchor delivery device 208 is typically used in conjunction with one or more additional laparoscopic instruments to perform the tissue reconfiguration procedures described herein. Several conventional laparoscopic instruments are known to those having ordinary skill in the art, and the details of those instruments are beyond the scope of the present description. FIG. 11 is an exemplary illustration of a laparoscopic instrument 310 having a shaft 312, an end effector 314, and a handle 316. In the embodiment shown, the instrument includes a substantially rigid shaft 312 and an end effector 314 in the form of a grasper having a pair of grasping jaws 320, 322. In FIGS. 12A-D, several alternative end effector embodiments are shown, including an alternative pair of grasping jaws 330, 332 shown in FIG. 12A, a pair of alligator grasper jaws 340, 342 shown in FIG. 12B, a pair of tong-style grasping members 350, 352 shown in FIG. 12C, and a blunt obturator 360 shown in FIG. 12D. Other optional laparoscopic instruments are suitable for use, including Babcock-style graspers, Maryland-style graspers, and other devices known to those skilled in the art.

Figure 13:
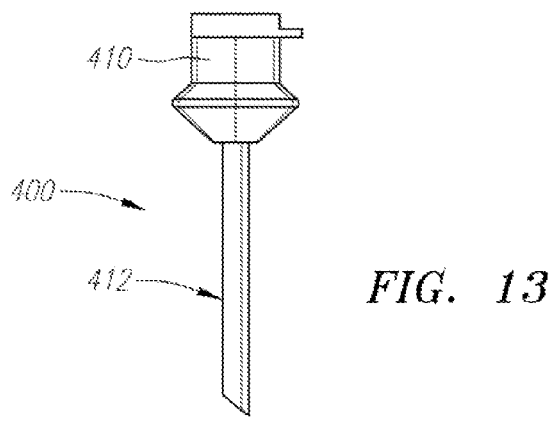
FIG. 13 is a side view of a trocar.

FIG. 13 illustrates a conventional trocar 400, including a cannula head portion 410 and a cannula tube portion 412.

Laparoscopic Treatment of Obesity

Referring to FIGS. 14-15, the anatomy of the stomach can be divided into different segments on the basis of the mucosal cell types and in relation to external anatomical boundaries. The cardiac segment C is immediately subjacent to the gastroesophageal junction GEJ and is a transition zone of the esophageal squamous epithelium into the gastric mucosa. The fundus F is the portion of the stomach that extends above the gastroesophageal junction. The body B or corpus of the stomach extends from the fundus F to the incisura angularis on the lesser curvature LC of the stomach. The majority of parietal acid forming cells are present in this segment. The fundus F and the body B function as the main reservoir of ingested food. The antrum A extends from the lower border of the body B to the pyloric sphincter PS. The majority of gastrin producing or G-cells are present in the antral mucosa. The main blood supply is variable but typically courses from the celiac axis into the gastric and gastroepiploic arcades. Nutrient vessels to the stomach course from the vascular arcades of the greater and lesser curvatures. These vessels penetrate the gastric wall in a perpendicular fashion and arborize horizontally in a dense vascular plexus throughout the wall of the stomach. For the most part, gastric innervation is provided by the vagus nerves which form a plexus around the esophagus and then reform into vagal trunks above the esophageal haitus. An extensive myenteric plexus is formed within the muscular wall of the stomach. Impulses from stretch or tension receptors within the gastric wall are transmitted to the nucleus tractus solitaris of the brain stem by afferent vagal fibers. These stretch/tension receptors within the fundus F and body B detect gastric distension or gastric pressure from ingested food.

The gastrointestinal lumen, including the stomach, includes four tissue layers, wherein the mucosa layer is the inner tissue layer followed by submucosa connective tissue, the muscularis layer and the serosa layer. When stapling or suturing from the peritoneal side of the GI tract, it is easier to gain access to the serosal layer. In endolumenal approaches to surgery, the mucosa layers are visualized, and the muscularis and serosal layers are difficult to access because they are only loosely adhered to the mucosal layer. In order to create a durable tissue fold or other approximation with suture or staples or some form of anchor, it is important to create a muscularis and/or serosa to serosa approximation. This is because the mucosa and submucosa connective tissue layers typically do not heal together in a way that can sustain the tensile loads imposed by normal movement of the stomach wall during ingestion and processing of food. In particular, folding the serosal layers in a way that they will heal together will form a durable tissue fold, plication, or elongated invagination.

Utilizing the instruments and systems described above in relation to FIGS. 1-13, various laparoscopic tissue reconfiguration and obesity-related procedures may be performed. For example, FIGS. 14-24 illustrate portions of the progression of a tissue reconfiguration and obesity treatment procedure being performed on a stomach. The remaining anatomy, including portions of the stomach S, has been omitted only for clarity.

Initially, one or more trocars 400 are inserted into the abdominal wall to provide access for the instruments into the peritoneal cavity and to the external surface of the stomach S. In some embodiments, a laparoscope is inserted through one of the trocars 400 in order to provide visualization and other possible functional features. Also, in some embodiments, the peritoneal cavity is insufflated to provide a desired amount of visualization and physical access to the external surface of the stomach S. Other suitable methods for providing and obtaining access to the external surface of the stomach S are also suitably employed.

As shown in FIG. 16, in some embodiments, an endoscope 500 or other device is inserted into the stomach of the patient transorally to provide visualization, insufflation, and/or other functions or features from within the interior space of the stomach S.

Once access to the external surface of the stomach is obtained, in some embodiments, the stomach S is mobilized by dissecting or partially dissecting the greater omentum along the greater curvature GC generally from the fundus F to the antrum A. (See FIG. 15). After mobilization, a large fold or invagination is formed in the stomach by pushing or pulling the tissue along the greater curvature GC into the interior of the stomach. For example, as shown in FIG. 18, a laparoscopic instrument 310 having a blunt obturator 360 may be used to push or poke the stomach. S along the greater curvature GC into the interior space of the stomach to thereby form a large internal invagination 508 of the greater curvature GC, which is also defined by a pair of large external tissue folds 510 and 512. Alternatively, a laparoscopic instrument 310 having a pair of grasping jaws 320, 322 or other end effector 314 may be used to form the invagination 508 at the greater curvature GC. In still other embodiments, a grasping laparoscopic instrument 310 may be used to grasp and pull or fold over the tissue near the locations of the external tissue folds 510 and 512 to form or assist in forming the large invagination 508 along the greater curvature GC. In still other embodiments, a combination of the foregoing instruments and methods are used to generally and substantially form the invagination 508 and the external tissue folds 510 and 512.

As shown in FIG. 17, in still other embodiments, an endoscopic grasper 502 or other retractor is optionally extended through a working channel of the endoscope 500 to grasp the internal surface of the stomach along the greater curvature GC and retract the tissue from inside the stomach. In embodiments in which the endoscope 500 is provided with a locking mechanism for the working channel, the grasper/retractor 502 may be locked in place to thereby hold the large invagination 508 in a fixed position while the procedure described below is undertaken. Moreover, the visualization functionality provided by the endoscope 500 provides the user with the capability of confirming the size, location, and relationship of the invagination 508 in relation to the interior of the gastrointestinal tract in order to assess the likely risk of obstruction or other complications.

Upon formation of the large invagination 508, or as the large invagination 508 is being formed, the tissue anchor delivery device 208 is deployed through a trocar 400 and the end effector 214 is brought near one of the external tissue folds 510 or 512, as shown in FIG. 19. In some embodiments, the launch tube 228 is retracted to open the space between the jaws 220, 222, which are then placed on either side of the tissue fold 512. In other embodiments, the tissue fold 510, 512 is retracted into the space between the jaws/bails 220, 222. The jaws 220, 222 are oriented on the tissue fold 512 such that the launch tube 228 is located between the tissue folds 510 and 512—thereby causing the tissue anchors 50a and 50b to be deployed on the exterior surfaces of the tissue folds 510, 512, as described in more detail below. The launch tube 228 is then advanced to close the jaws 220, 222 on the tissue fold 512, after which the needle deployment assembly 260 is actuated to cause the needle 272 to extend through the tissue fold 512. In the embodiment shown, the distal anchor 50a is then deployed from the needle 272. The needle 272 is then retracted back into the needle deployment assembly 260, leaving the distal anchor 50a deployed against the surface of the tissue fold 512 and the suture 60 extending through the tissue fold 512. The launch tube 228 is then retracted, the jaws 220, 222 opened, and the tissue fold 512 is released from the delivery device 208.

Next, turning to FIG. 20, the delivery device 208 is "flipped" along its axis and is moved to the other tissue fold 510, as shown in FIG. 20. The suture 60 is paid out from the needle deployment assembly 260 through the needle 272 as the delivery device 208 is moved. Once in position, the delivery device 208 is closed upon the other tissue fold 510 and the proximal anchor 50b and cinch 102 of the anchor assembly 100 are deployed through the other tissue fold 510. After deployment, the launch tube 228 is retracted, the jaws 220, 222 opened, and the tissue fold 510 is released from the delivery device 208. At this point, the suture 60 of the anchor assembly 100 extends through the tissue folds 510, 512 and is loosely held in place by the distal anchor 50a, distal anchor 50b, and cinch 102.

Figure 21:
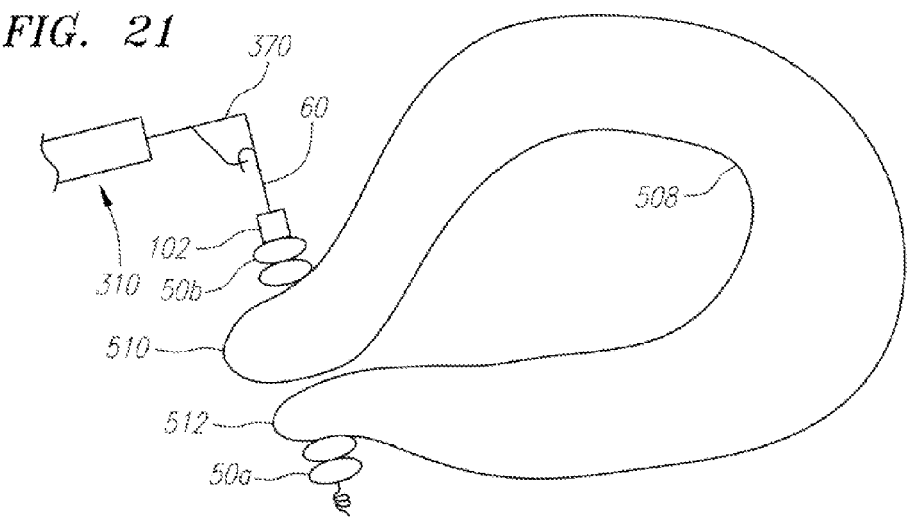
Figure 22:
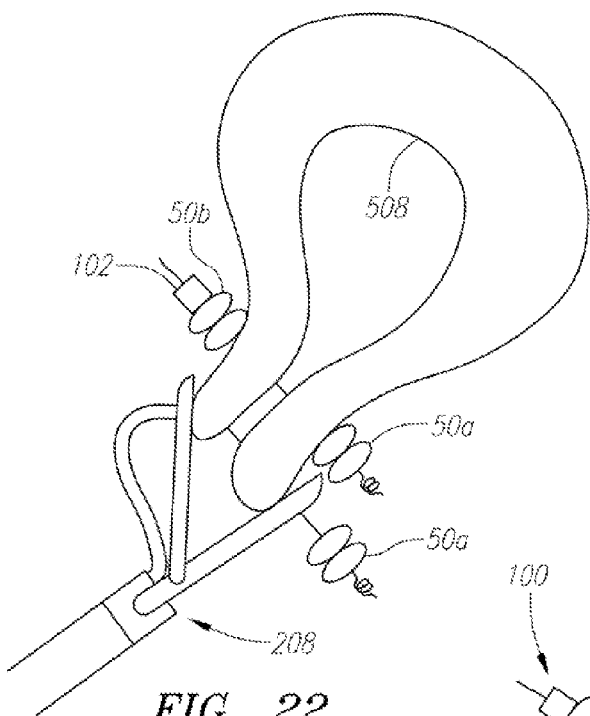
Figure 23:
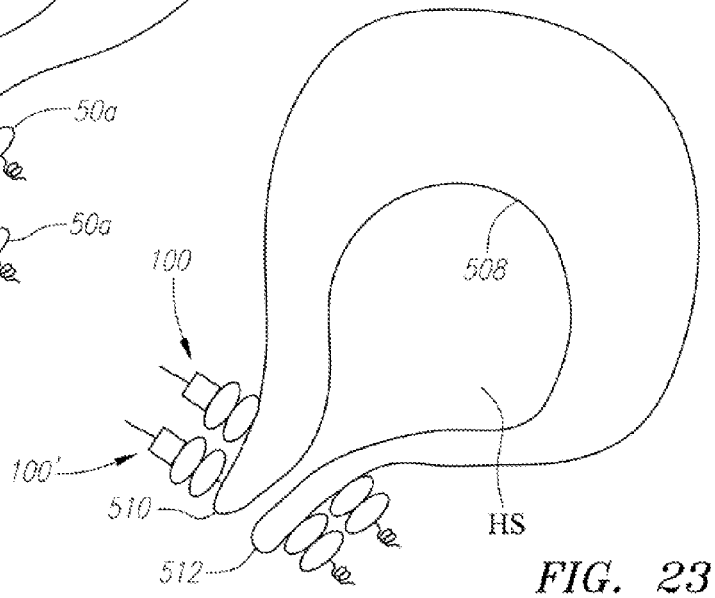
Figure 24:
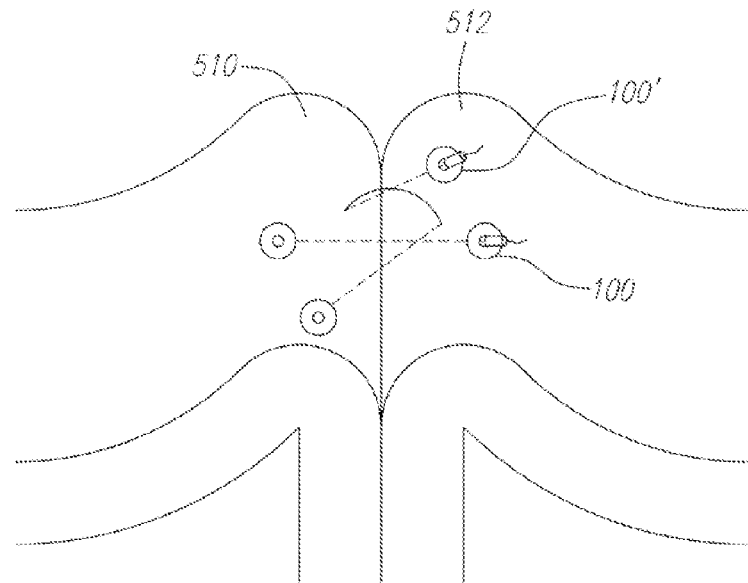
FIG. 24 is a perspective view of a portion of stomach tissue showing a first tissue anchor assembly apposing a pair of tissue folds and a second tissue anchor assembly in a figure-of-eight orientation reinforcing the first tissue anchor assembly.

Turning to FIG. 21, a laparoscopic instrument 310 is provided having an end effector 314 suitable for cinching the anchor assembly deployed through the tissue folds 510 and 512 in the procedures described above. Examples of end effectors for cinching instruments are described in U.S. patent application Ser. Nos. 12/054,297 and 10/954,665, which are hereby incorporated by reference in their entireties. Suitable end effectors include a simple pair of grasping jaws, a finger snare, or other mechanism. In the embodiment shown, the laparoscopic instrument 310 includes a finger snare 370 adapted to acquire and grasp the suture 60, and to apply a tension force upon the suture 60 to thereby slide the unidirectional cinch 102 up against the proximal anchor 50b. This action shortens the length of suture 60 between the proximal anchor 50b and distal anchor 50a, thereby bringing the tissue folds 510 and 512 into apposition.

Figure 30A:
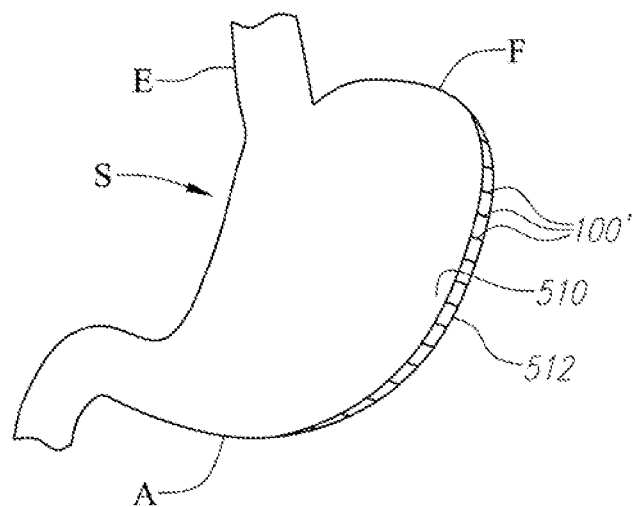
FIGS. 30A-B are anterior side views of a human stomach after undergoing a laparoscopic tissue reconfiguration.

The foregoing method steps are repeated at several locations along the greater curvature GC between the fundus F and antrum A of the stomach S until the large invagination 508 extends through all or most of the length of the stomach S, as shown, for example, in FIG. 30A. For example, in some embodiments, additional tissue anchor assemblies 100 are deployed along the greater curvature 100 at intervals of approximately 0.5 cm to about 2 cm, or sufficiently near each other to avoid gaps large enough that the tissue folds 510 and 512 will not heal together. In addition, although the illustrations shown in FIGS. 19-23 show an open or hollow space HS formed within the interior of the invagination 508, it is believed that the tissue surfaces opposing one another within the space HS will be in contact with each other and will reform or remodel due to the reconfiguration created by the foregoing method steps.

Figure 31:
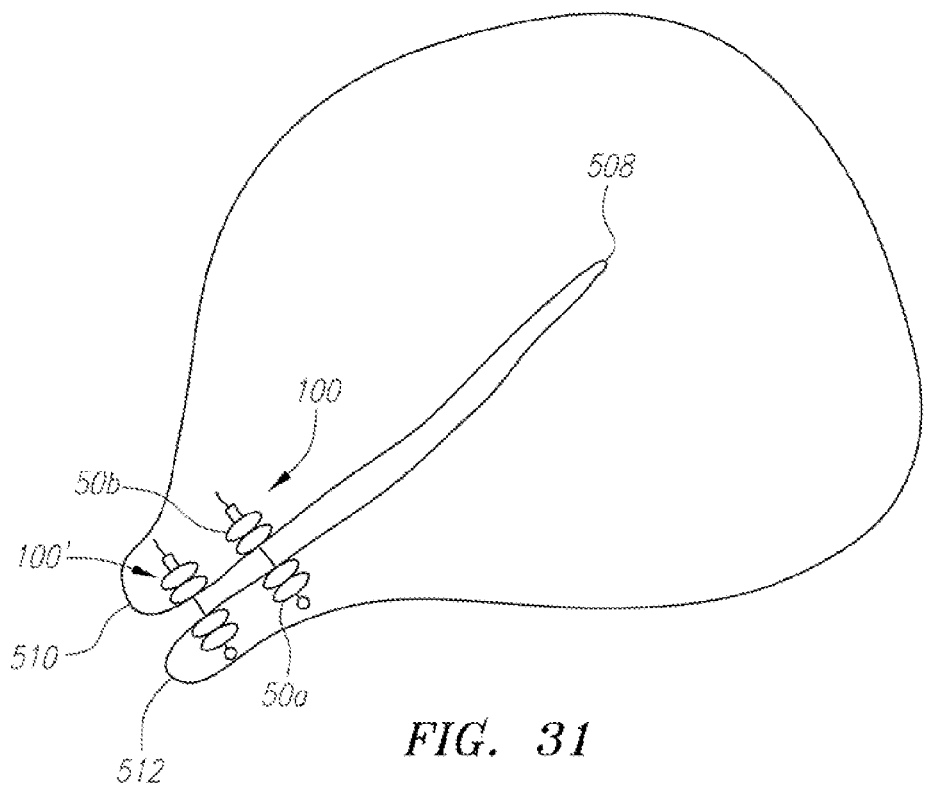
FIGS. 31 and 32 are cross-sectional top views taken along line D-D of the human stomach shown in FIG. 14 illustrating alternative embodiments of a laparoscopic stomach tissue reconfiguration procedure.
Figure 32:
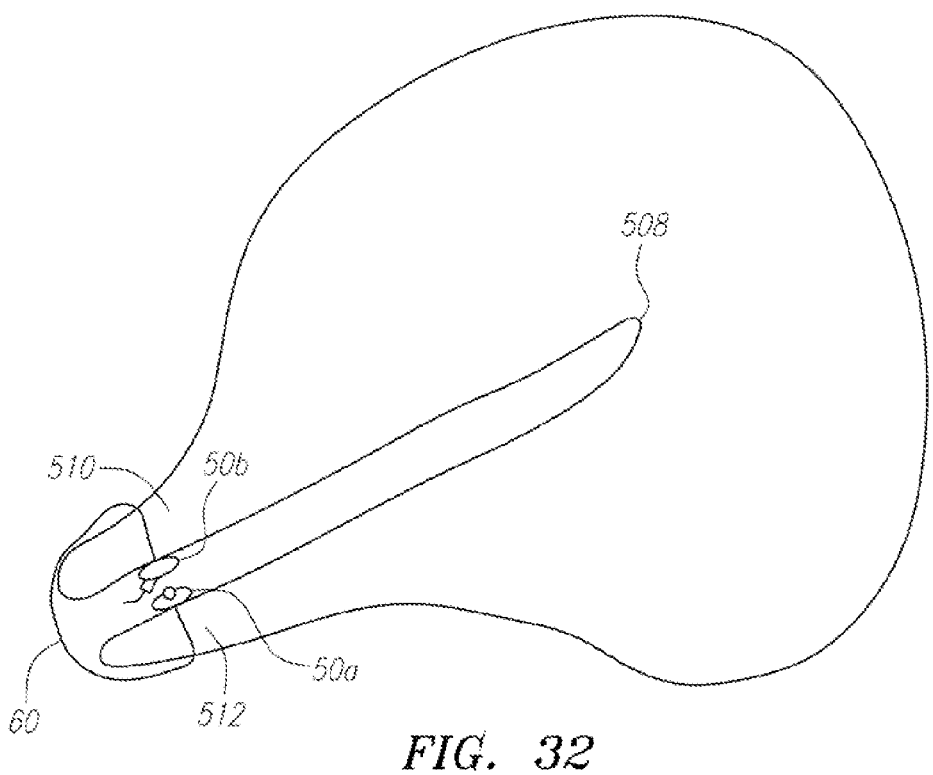

In some alternative embodiments, one or both of the tissue anchors 50a, 50b are deployed through only a single layer of the tissue folds 508, 510, such that the tissue anchors 50a, 50b are located on the interior of the stomach. (See FIG. 31). In some other alternative embodiments, one or both of the tissue anchors 50a, 50b are deployed such that the anchors 50a, 50b are located between the tissue folds 510, 512 after the tissue folds are approximated toward one another by the tissue anchor assemblies 100. In these embodiments, the delivery device 208 is located upon the tissue folds 510, 512 and the tissue anchors 50a, 50b are deployed through the tissue folds 510, 512 in the opposite direction to the embodiment discussed above in relation to FIGS. 19-20. Once the anchor assemblies 100, 100' are fully deployed and the anchors 50a, 50b are cinched together, the tissue folds 510, 512 are brought into apposition in the manner shown in FIG. 32.

After the full stomach has been reconfigured according to the above procedures, in some embodiments additional tissue anchor assemblies 100' are deployed to provide further strength to the reconfigured tissue folds 508, 510, and/or 512. For example, in FIGS. 22-23 there is shown an additional reinforcing tissue anchor assembly 100' that is deployed in a single plication deployment using the tissue anchor deployment device 208 deployed through the pair of tissue folds 510 and 512. In other embodiments, the additional tissue anchor assembly 100' is deployed in a Figure-of-Eight deployment (see FIG. 24) or using the tissue fold-apposition deployment method described above in relation to FIGS. 19-21 and/or FIGS. 31-32. Other deployment methods are also contemplated and are possible. In still other embodiments, the reconfigured tissue folds 508, 510, and/or 512 are reinforced by oversewing using a running stitch, an interrupted stitch, or other method(s) using the laparoscopic instruments described herein, or other instruments known to those skilled in the art. In still other embodiments, the reconfigured tissue folds 508, 510, and/or 512 are approximated and/or reinforced using staples, clips, or other fasteners known to those skilled in the art.

Figure 25A:
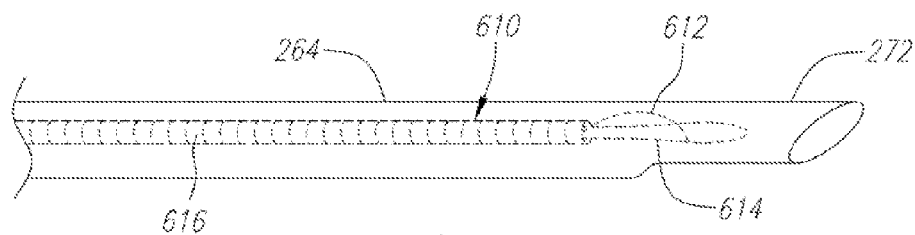
FIGS. 25A-B are side cross-sectional and side views, respectively, of a snare-type suture grasping device.
Figure 25B:
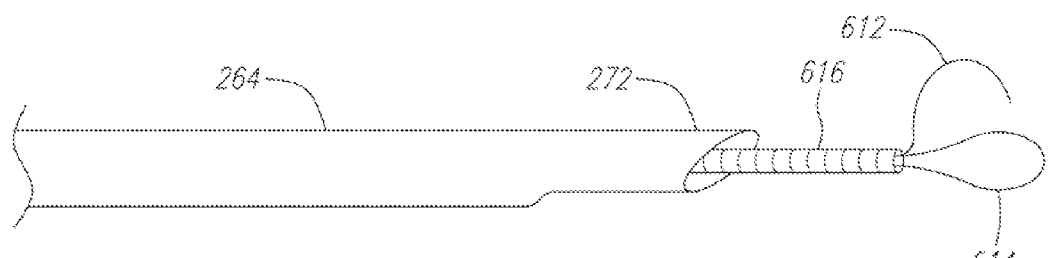

Turning to FIGS. 25A-B, 26A-G, and 27A-B, there are shown devices and methods for laparoscopic suturing that are particularly adapted to the present tissue reconfiguration methods. For example, FIGS. 25A-B show a suture grasping device snare-style grasper 610 having a hook 612 and an eyelet 614 attached to the distal end of an elongated shaft 616. The snare-style grasping device 610 is adapted to be slidably and rotatably retained within, for example, a flexible sheath 264 and needle body 272 of, for example, the tissue anchor deployment device 208 described above in relation to FIGS. 3-10. The Figures illustrate the distal portion of a sheath 264 and needle body 272 along with the snare device 610. The remaining portions of the delivery device 208 have been omitted only for clarity.

As the snare is extended out of the distal end of the needle body 272, the hook 612 expands upward away from the eyelet 614, and the eyelet expands outward 614 away from the hook 612, thereby defining an open space between the hook 612 and eyelet 614. (See FIG. 25B). When the snare is retracted back into the needle body 272 and sheath 264, (see FIG. 25A), the hook 612 collapses into the eyelet 614, trapping anything (e.g., a suture 660) placed within the open space when it was open. In this way, the deployment device 208 may be used to perform laparoscopic suturing, as described in more detail below.

Figure 26A:
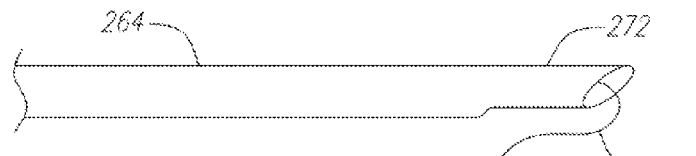
FIGS. 26A-G are illustrations of the progression of a method for laparoscopic suturing.
Figure 26B:
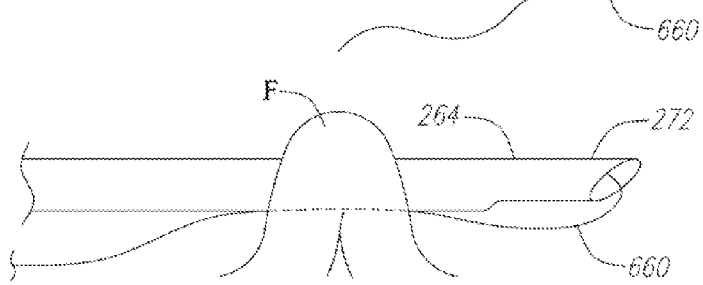
Figure 26C:
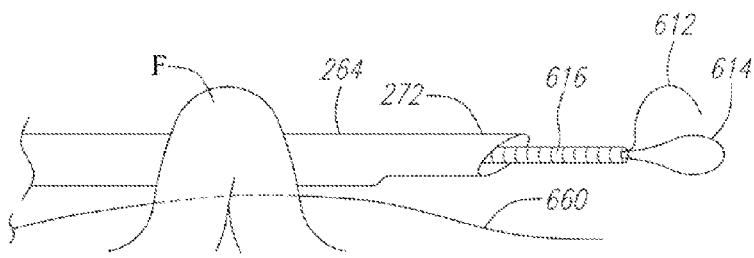
Figure 26D:
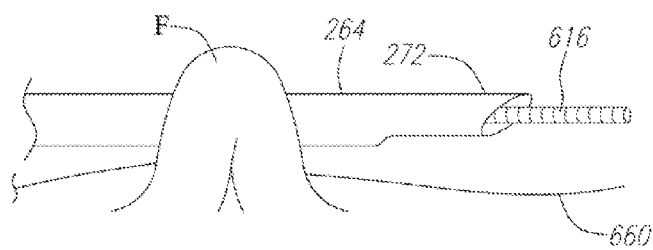
Figure 26E:
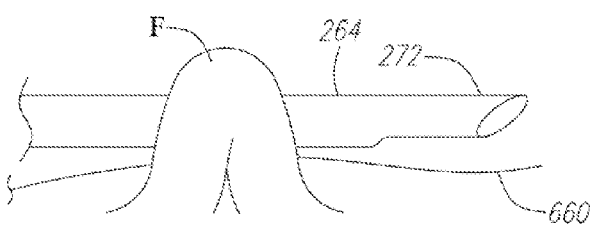
Figure 26F:
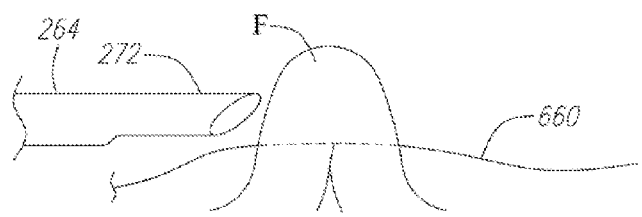
Figure 26G:
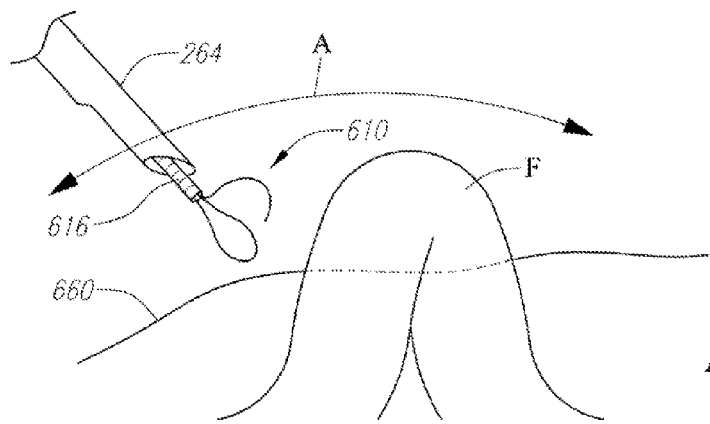

In FIG. 26A, a snare device (not shown) is slidably retained within a sheath 264 and needle body 272 of a deployment device (also not shown). The snare device has captured a portion of suture 660 and retracted it into the sheath 264. The needle body 272 is then pierced through a tissue fold F, carrying with it the suture 660, as shown in FIG. 26B. After advancement of the needle 272 and sheath 264 through the tissue fold, the snare device 610 is advanced distally by advancing the elongated shaft 616, thereby expanding the hook 612 and eyelet 614 and releasing the suture 660. (See FIG. 26C). The snare device 610 is then retracted back into the sheath 264, (FIGS. 26D-E), and the sheath 264 is withdrawn from the tissue fold F, (FIG. 26F). This leaves the suture 660 extending through the tissue fold F, and leaves the user with the snare device 610 in position to perform another operation. As shown by the arrow "A" in FIG. 26G, the elongated shaft 616 may be extended to expose the snare device 610 to grasp the suture 660 on either side of the tissue fold F. Once grasped, the process may be repeated any number of times in order to route the suture 660 through the tissue fold F and thereby perform a suturing procedure.

Figure 27A:
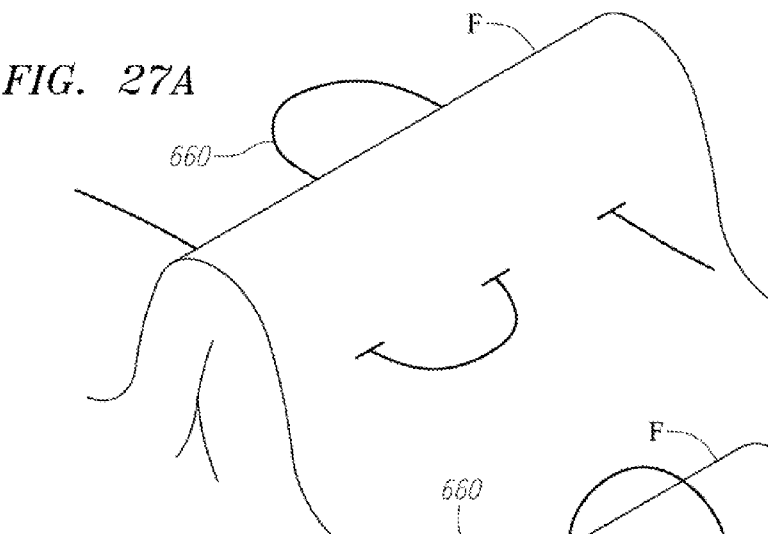
FIGS. 27A-B are illustrations of running stitches applied using the method shown in FIGS. 26A-G.
Figure 27B:
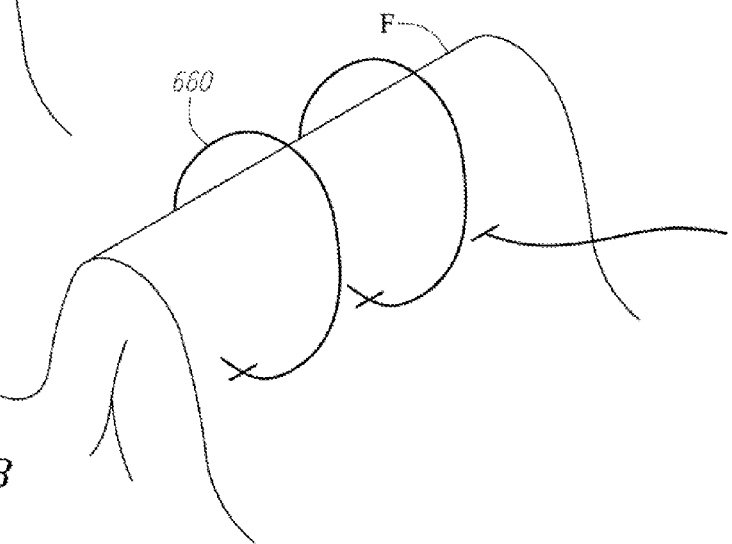

FIGS. 27A and 27B illustrate two examples of running stitches that are applied laparoscopically to tissue using the deployment device 208 carrying the snare device 610 described herein. The laparoscopic suturing procedures may be completed by securing the suture ends with tissue anchors described herein, or by other methods known to those skilled in the art. For example, the suture ends may be secured by tying knots in the suture 660 or by passing one or more suture knots via a knot pusher, by applying a clip or other securing device to the suture 660 using a clip applier or similar device, or by other means. In other embodiments, a barbed suture 660 is used to thereby eliminate the need for separately securing the suture.

Turning to FIGS. 28A-D and 29A-F, in some embodiments, the needle deployment assembly 260 provided in the tissue anchor delivery device 208 with an anchor retention mechanism that facilitates deployment of a single anchor of a tissue anchor assembly 100 (such as the distal anchor 50a shown in FIG. 19) without inadvertently deploying both anchors of the assembly. FIGS. 28A-D and 29A-F illustrate the distal portion of a sheath 264 and needle body 272 of a needle deployment assembly 260. The remaining portions of the delivery device 208 have been omitted only for clarity.

Figure 28A:
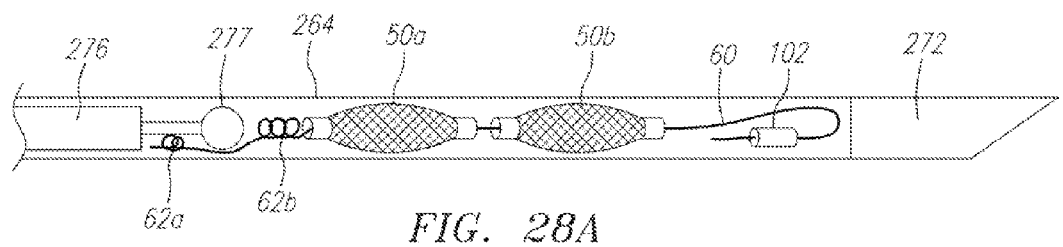
FIGS. 28A-D are side cross-sectional view of four embodiments of an anchor retention mechanism.

In the embodiment shown in FIG. 28A, the elongate pusher 276 is provided with an extension arm 277 having an enlarged portion at its distal end. The enlarged portion of the extension arm 277 traps a first knot 62a formed at a proximal end of the suture of the tissue anchor assembly 100 within the interior space of the sheath 264. A second knot 62b formed distally of the first knot 62a is attached (e.g., with glue or other adhesive) to the distal anchor 50a, thereby providing the pusher 276—to which the extension arm 277 is attached—with the capability of positively controlling the position of the distal anchor 50a within the sheath 264. Accordingly, as the pusher 276 is advanced distally within the sheath 264, the distal anchor 50a (and the components that are within the sheath 264 distal of the distal anchor) will be advanced distally. As the pusher 276 is retracted proximally within the sheath 264, the distal anchor 50a will be retracted proximally. This capability reduces the possibility that the distal anchor 50a will be deployed inadvertently.

Figure 28B:
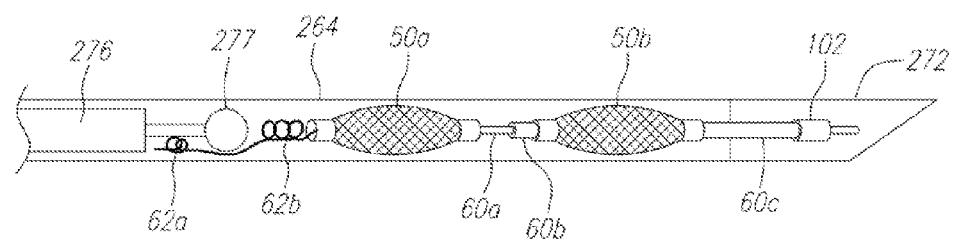

The embodiment shown in FIG. 28B is similar to the one shown in FIG. 28A, except rather than having the distal anchor 50a being adhered to the second knot 62b, the distal anchor 50a is prevented from moving distally relative to the suture 60 by the inclusion of a step up in thickness of the suture relative to the diameter of the passageway through the distal anchor 50a. For example, the suture has a first thickness at region 60a that is small enough that the distal anchor 50a is able to slide freely back and forth along the suture 60a. However, at region 60b, the suture has a thickness that is larger, such that the distal anchor 50b is not able to traverse the transition from region 60a to region 60b. In this way, the distal anchor 50a is thereby trapped within a pre-determined region of travel by the elongate pusher 276, thereby reducing the possibility that the distal anchor 50a will be deployed inadvertently.

Figure 28C:
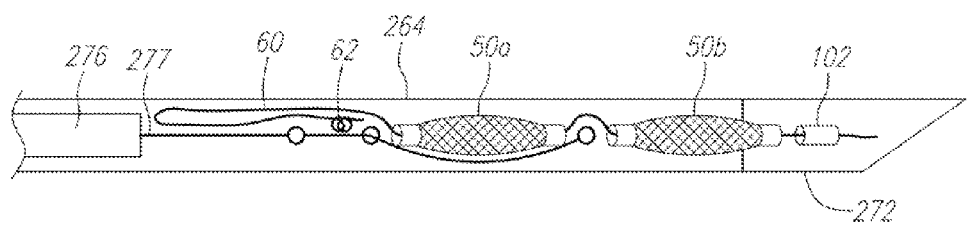
Figure 28D:
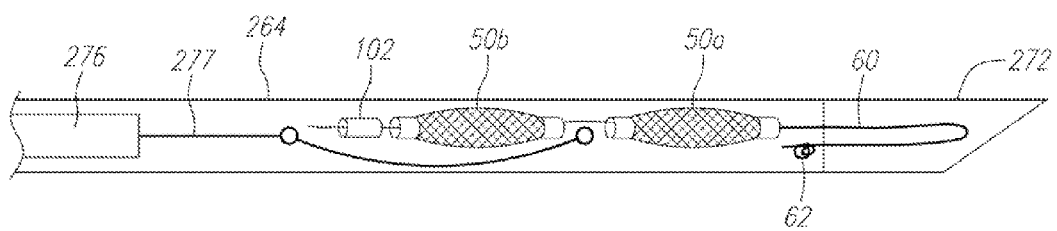

In the embodiments shown in FIGS. 28C and 28D, the extension arm 277 includes a region that physically traps the entire distal anchor 50a, thereby directly controlling the location of the distal anchor with the pusher 276.

Figure 29A:
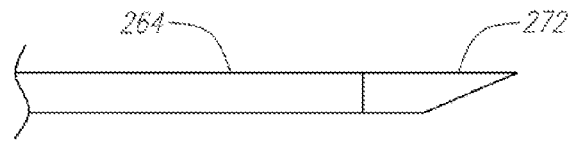
FIGS. 29A-F are illustrations of the progression of an anchor deployment method using an anchor retention mechanism.
Figure 29B:
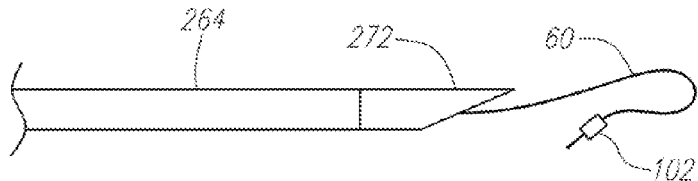
Figure 29C:
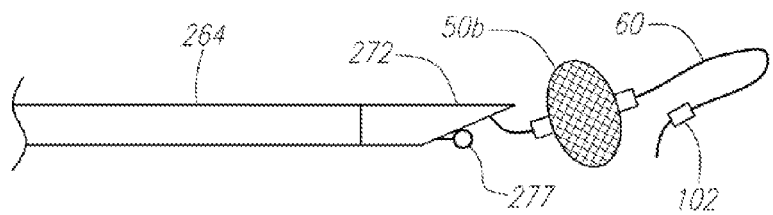
Figure 29D:
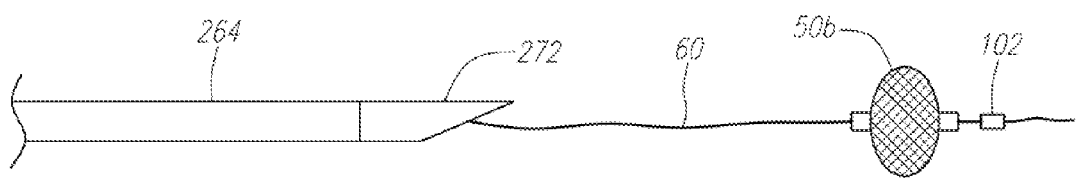
Figure 29E:
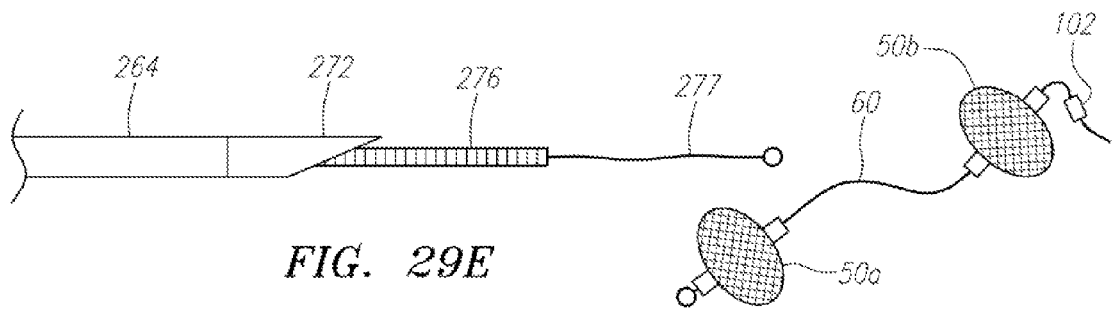
Figure 29F:
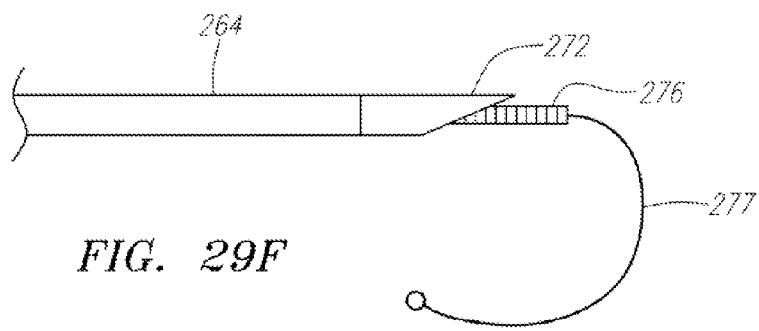

Turning to FIGS. 29A-F, the manner of operation of the retention mechanisms described above is shown. A needle 272 and sheath 264 of a needle deployment assembly 260 are deployed from a tissue anchor deployment device 208. As the pusher 276 is advanced, the cinch 102 and suture 60 are expelled from the distal end of the needle body 272, as shown in FIG. 29B. Further advancement of the pusher 276 causes the proximal anchor 50b to be expelled. (See FIG. 29C). In FIG. 29C, the enlarged distal end of the extension arm 277 is seen extending from the distal opening of the needle body 272, but the distal anchor 50a remains held within the sheath 264. As the deployment device 208 is retracted, such as when the device is moved to the location of a second tissue fold, the suture 60 is paid out, as shown in FIG. 29D. Finally, the pusher 276 is fully extended outside of the sheath 264 and needle body 272, thereby releasing the distal anchor 50a. (See FIG. 29E). In an alternative embodiment, the extension arm 277 is provided with a shape memory curve, (see FIG. 29F), to prevent inadvertent engagement or interference with the target tissue.

Figure 30B:
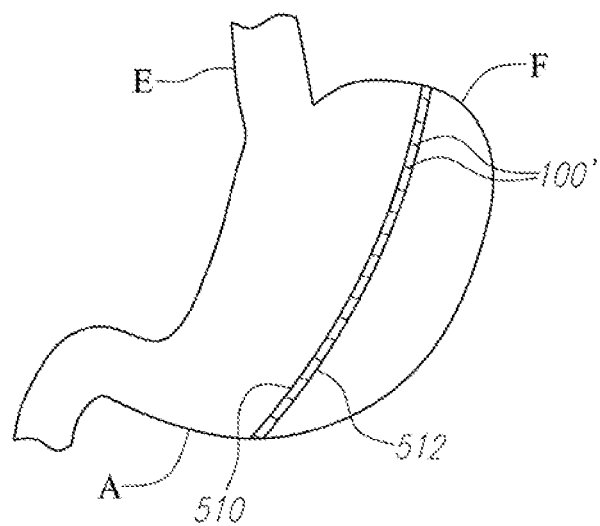

The described methods include several embodiments, including all of the embodiments described herein as well as all combinations of each of those embodiments. Additional combinations of the therapeutic methods described herein will obtain similar results. In addition, other versions of the foregoing methods have been contemplated and are within the scope of the present methods. For example, the large invagination 508 may be formed at locations on the stomach other than on or near the greater curvature 508 shown in FIG. 30A, such as along the anterior wall of the patient's stomach, as shown in FIG. 30B. In other embodiments, invaginations are formed at multiple locations on the stomach. In addition, the invaginations may be provided having smaller or larger sizes than those shown in the embodiments described herein.

Although various illustrative embodiments are described above, it will be evident to one skilled in the art that various changes and modifications are within the scope of the invention. It is intended in the appended claims to cover all such changes and modifications that fall within the true spirit and scope of the invention.

What is claimed is:

1. A laparoscopic method for reconfiguring tissue of a hollow organ within the body of a patient, comprising:
   positioning a launch tube containing a needle outside of an external surface of the hollow organ;
   forming a first tissue fold on the external surface of the hollow organ by advancing the launch tube to operate a jaw member, with the first tissue fold having an inner side and an outer side;
   extending the needle out of the launch tube and piercing through the first tissue fold with the needle by inserting the needle into the inner side of the first tissue fold, and with the needle projecting out from the outer side of the first tissue fold, with the needle containing a first anchor assembly having a first anchor connected to a second anchor by a connecting member;
   deploying the first anchor from the needle on the outer side of the first tissue fold by pushing the first anchor out of the needle;
   withdrawing the needle from the first tissue fold;
   forming a second tissue fold on the external surface of the hollow organ by advancing the launch tube to operate the jaw member, with the second tissue fold having an inner side and an outer side, and with the inner side of the first tissue fold facing the inner side of the second tissue fold;
   extending the needle out of the launch tube and piercing through the second tissue fold with the needle by inserting the needle into the inner side of the second tissue fold, and with the needle projecting out from the outer side of the second tissue fold;
   deploying the second anchor from the needle on the outer side of the second tissue fold by pushing the second anchor out of the needle; and
   moving at least one of the first anchor or second anchor along the connecting member to approximate the first and second tissue folds.

2. The method of claim 1, further comprising deploying a second anchor assembly into the first and second tissue folds.

3. The method of claim 1, further comprising deploying a plurality of additional anchor assemblies into the first and second tissue folds.

4. The method of claim 1 further comprising piercing the first tissue fold with the needle substantially perpendicular to an axis of the jaw member.

5. The method of claim 1 further comprising piercing the first tissue fold by extending a tip of the needle through an opening in the jaw member.

6. The method of claim 1 wherein the tissue folds are external tissue folds.

7. A laparoscopic method for performing surgery on an organ of a patient, comprising:
   forming a first external tissue fold by grasping and holding an external surface of the organ by advancing a launch tube outside of the organ to operate a jaw member;
   extending a needle out of the launch tube and piercing the first external tissue fold, with the needle containing a first anchor assembly having a first anchor connected to a second anchor by a connecting member;
   deploying the first anchor by pushing it out of the needle;
   withdrawing the needle from the first external tissue fold;
   forming a second external tissue fold by grasping and holding an external surface of the organ at a position spaced apart from the first anchor by advancing the launch tube outside of the organ to operate the jaw member;
   extending the needle out of the launch tube and piercing the second external tissue fold;
   deploying a second anchor by pushing it out of the needle;
   withdrawing the needle from the second external tissue fold; and
   moving at least one of the first anchor or second anchor along the connecting member to approximate the first and second tissue folds.

8. The method of claim 7 with the connecting member comprising suture.

9. The method of claim 8 further comprising moving a cinch along the suture to hold the first and second tissue folds.

10. The method of claim 7 with the connecting member comprising suture and further including moving at least one of the first and second anchors along the suture.

11. The method of claim 7 further comprising piercing the first external tissue fold with the needle substantially perpendicular to an axis of the jaw member.

12. The method of claim 7 further comprising piercing the first external tissue fold by extending a tip of the needle through an opening in the jaw member.

13. The method of claim 7 with the launch tube on a surgical tool having and axis, further comprising flipping the surgical tool about its axis after withdrawing the needle from the first tissue fold.

* * * * *